(12) United States Patent
Atterbury et al.

(10) Patent No.: US 7,849,850 B2
(45) Date of Patent: Dec. 14, 2010

(54) NOZZLE FOR HANDHELD PULMONARY AEROSOL DELIVERY DEVICE

(75) Inventors: William G. Atterbury, Columbus, OH (US); Chad E. Bouton, Delaware, OH (US); David R. Busick, Lewis Center, OH (US); James E. Dvorsky, Norwich Township, OH (US); Peter A. Gaydos, Hilliard, OH (US); David A. Holley, Lancaster, OH (US); Daniel D. Meek, Canal Winchester, OH (US); Gregory A. Trees, Columbus, OH (US)

(73) Assignee: Battelle Memorial Institute, Columbus, OH (US)

( * ) Notice: Subject to any disclaimer, the term of this patent is extended or adjusted under 35 U.S.C. 154(b) by 960 days.

(21) Appl. No.: 10/375,957

(22) Filed: Feb. 28, 2003

(65) Prior Publication Data

US 2004/0195403 A1 Oct. 7, 2004

(51) Int. Cl.
*A61M 11/00* (2006.01)
*B05B 5/00* (2006.01)
*F23D 11/32* (2006.01)
(52) U.S. Cl. .................... 128/200.14; 239/692
(58) Field of Classification Search ............ 128/200.14, 128/200.16, 200.23, 203.12, 203.24, 204.25; 239/692; 427/483
See application file for complete search history.

(56) References Cited

U.S. PATENT DOCUMENTS 4,004,733 A * 1/1977 Law ............................ 239/3
4,356,528 A 10/1982 Coffee ........................ 361/226
4,358,059 A 11/1982 Coffee (Continued)

FOREIGN PATENT DOCUMENTS

EP 0 054 730 6/1982

(Continued)

OTHER PUBLICATIONS

Cloupeau, M. et al.; "Electrohydrodynamic Spraying Functioning Modes: A Critical Review"; J Aerosol Sci.; 1994; 25(6); pp. 1021, 1025-1026.

(Continued)

*Primary Examiner*—Justine R Yu
*Assistant Examiner*—Kristen C Matter
(74) *Attorney, Agent, or Firm*—Stevens & Showalter LLP

(57) ABSTRACT

An improved Electrohydrodynamic (EHD) nozzle particularly suitable for a handheld pulmonary aerosol inhaler increases the consistent and efficient dispensing of therapeutic liquids by reducing or eliminating wetting through shielding of discharge electrodes. Some versions further eliminate wetting while enhances neutralization of the aerosol through presentation of a corona wind of ions annularly surround the aerosol. Incorporation of improved liquid distribution with consistent pressure drops to each EHD nozzle tip allows horizontal dispensing, and by using dielectric nozzle tips with low surface energy to thereby avoid wicking between dispenses and to advantageously reduce achievable particle size when dispensing. Some versions feature enhanced snap-fit assembly and other manufacturability advantages. One of the unique features of the EHD nozzles is achieved high dose rate (microliters/minute) with low wetting and small particle size (1.0-5 microns), although these properties tend to be mutually exclusive. Furthermore, these attributes are incorporated into a conveniently small, handheld device.

27 Claims, 16 Drawing Sheets

U.S. PATENT DOCUMENTS

| | | | |
|---|---|---|---|
| 4,362,775 A | 12/1982 | Yabe et al. ................... 428/213 |
| 4,470,550 A | 9/1984 | Coffee |
| 4,549,243 A | 10/1985 | Owen et al. |
| 4,561,037 A | 12/1985 | MacLaine et al. |
| 4,634,057 A | 1/1987 | Coffee et al. |
| 4,659,012 A | 4/1987 | Coffee ........................... 239/3 |
| 4,663,639 A | 5/1987 | Owen et al. |
| 4,703,891 A | 11/1987 | Jackson et al. |
| 4,801,086 A | 1/1989 | Noakes |
| 4,829,996 A * | 5/1989 | Noakes et al. ........... 128/200.14 |
| 4,962,885 A | 10/1990 | Coffee |
| 5,044,564 A * | 9/1991 | Sickles ................... 239/690.1 |
| 5,121,884 A | 6/1992 | Noakes |
| 5,184,778 A | 2/1993 | Noakes |
| 5,222,663 A | 6/1993 | Noakes et al. |
| 5,222,664 A | 6/1993 | Noakes et al. |
| 5,704,554 A * | 1/1998 | Cooper et al. ............ 239/690.1 |
| 5,788,166 A | 8/1998 | Valaskovic et al. |
| 5,810,265 A | 9/1998 | Cornelius et al. |
| 5,927,618 A | 7/1999 | Jefferies et al. |
| 5,932,011 A | 8/1999 | Noakes et al. |
| 6,068,199 A | 5/2000 | Coffee |
| 6,079,634 A | 6/2000 | Noakes et al. |
| 6,105,571 A | 8/2000 | Coffee |
| 6,138,671 A | 10/2000 | Noakes et al. |
| 6,145,391 A | 11/2000 | Pui et al. |
| 6,286,725 B1 | 9/2001 | Gerber |
| 6,302,331 B1 * | 10/2001 | Dvorsky et al. ................. 239/3 |
| 6,311,903 B1 | 11/2001 | Gaw et al. |
| 6,318,640 B1 | 11/2001 | Coffee |
| 6,318,647 B1 | 11/2001 | Gaw et al. |
| 6,368,079 B2 | 4/2002 | Peters et al. |
| 6,386,195 B1 * | 5/2002 | Coffee .................... 128/200.14 |
| 6,397,838 B1 * | 6/2002 | Zimlich et al. ......... 128/200.14 |
| 6,454,193 B1 * | 9/2002 | Busick et al. ............... 239/690 |
| 6,457,470 B1 | 10/2002 | Coffee .................... 128/200.14 |
| 6,491,897 B1 | 12/2002 | Freund et al. |
| 6,503,481 B1 * | 1/2003 | Thurston et al. ............... 424/45 |
| 6,595,208 B1 * | 7/2003 | Coffee et al. ............ 128/203.12 |
| 6,660,715 B2 | 12/2003 | Klibanov |
| 6,684,879 B1 | 2/2004 | Coffee et al. ........... 128/200.14 |
| 6,796,303 B2 * | 9/2004 | Zimlich et al. ......... 128/200.14 |
| 6,827,559 B2 | 12/2004 | Peters et al. |
| 6,880,554 B1 | 4/2005 | Coffee .................... 128/200.14 |
| 2003/0216471 A1 * | 11/2003 | Dahl et al. ................... 514/559 |
| 2004/0001655 A1 | 1/2004 | Proicou et al. |
| 2004/0195403 A1 | 10/2004 | Atterbury et al. |
| 2006/0261179 A1 | 11/2006 | Davies et al. |
| 2008/0308095 A1 | 12/2008 | Trees et al. |
| 2008/0308580 A1 | 12/2008 | Gaydos et al. |

FOREIGN PATENT DOCUMENTS

| | | |
|---|---|---|
| GB | 261827 | 11/1926 |
| GB | 2 018627 | 10/1979 |
| WO | WO 99/07478 | 2/1999 |
| WO | 03072263 | 9/2003 |
| WO | 2004054627 A1 | 7/2004 |
| WO | WO 20074/078244 | 9/2004 |
| WO | 2007094835 A1 | 8/2007 |

OTHER PUBLICATIONS

International Search Report No. PCT/US2006/044626; Mar. 26, 2007.

* cited by examiner

NOZZLE FOR HANDHELD PULMONARY AEROSOL DELIVERY DEVICE

FIELD OF THE INVENTION

This invention relates to devices and methods for delivering an aerosolized liquid to a user's lungs, and particularly an aerosolized liquid having therapeutic properties.

BACKGROUND OF THE INVENTION

Inhalation therapy for delivering both locally/topically and systemically active drug compounds is increasing as the health-care community recognizes the benefits this route offers to patients. For some therapeutic agents, delivery of the aerosolized liquid without a propellant is preferred. Such liquids may be aerosolized, for example, by an electrohydrodynamic (EHD) apparatus. EHD aerosol delivery systems are expected to revolutionize inhalation therapy. These novel systems are more efficient and reproducible than existing inhalation devices. EHD devices can deliver a soft (isokinetic) cloud of uniformly sized particles directly to the lungs with better than 90 percent efficiency, and without the need for liquid propellants or other pressurized systems. The aerosol is delivered using the patient's own breath (inspiration), whereby the patient can easily achieve the drug delivery at normal inhalation rates. The delivery mechanism is especially suited to use with infants, young children, seniors, and patients with an impaired respiratory function.

A net electric charge is imparted to the fluid by putting a charged electrode in the fluid path. The liquid to be aerosolized is made to flow through a region of high electric field strength. This fluid charge tends to remain on the surface of the liquid such that, as the liquid exits the nozzle, the repelling force of the surface charge balances against the surface tension of the liquid, forming a cone (a "Taylor cone" as described in, e.g., M. Cloupeau and B. Prunet-Foch, "Electrohydrodynamic Spraying Functioning Modes: A Critical Review," J Aerosol Sci., Vol. 25, No. 6, pp. 1021, 1025-1026 (1994)). In the region of the tip of the cone, which has the greatest charge concentration, the electrical force exerted on the liquid surface overcomes the surface tension, generating a thin jet of liquid. The jet breaks into droplets of more or less uniform size, which collectively form a cloud that may be inhaled by a user to deliver the aerosol to the user's lungs.

It is generally known to aerosolize pharmaceutical formulations and discharge the aerosol particles prior to their delivery to a user. One such method uses an electrohydrodynamic apparatus having a single spray site (nozzle tip) surrounded by discharge electrodes and a grounded shield to produce a monodispersed spectrum of particle sizes. Although these known approaches produce an aerosolized liquid, they have a number of disadvantages.

Generally known pulmonary delivery devices that use electrohydrodynamic spraying are unwieldy and require connection to either an alternating current power supply or a large direct current power supply. These conventional devices are suitable for use in hospital or other clinical applications, such as for administering a therapeutic agent during a scheduled treatment appointment, but generally are not suitable for use directly by a user on a demand or as-needed basis outside a clinical setting. Conventional devices are particularly unsuited for use during a user's regular activities at home, at work, while traveling, and during recreational and leisure activities.

Known pulmonary delivery devices that use electrohydrodynamic spraying also lack a sufficient volumetric flow rate to deliver a desired amount of certain therapeutic liquids during the inhalation of one to two breaths by a user. Attempts to increase the flow rate generally have resulted in even more bulky devices unsuitable for hand-held use. These delivery devices also are not generally capable of spraying liquids having a broad range of conductivities.

The commonly-owned U.S. Pat. No. 6,397,838 to Zimlich, Jr., et al., which is hereby incorporated by reference in its entirety, discloses a pulmonary aerosol delivery device that delivers an aerosolized liquid cloud having therapeutic properties to a user's lungs. The compact and convenient device includes a housing of such size that it can be held in a user's one hand with an exit opening in the housing for directing the aerosol to the user's mouth. The aerosolizing apparatus (i.e., EHD nozzle) includes a plurality of spray sites (i.e., tip ends) that cooperate with discharge electrodes and reference electrodes downstream respectively of the tip ends to result in an aerosolized spray from at least one tip end. The multiple spray sites can achieve larger dosages.

While U.S. Pat. No. 6,397,838 presents a significant advance over generally known aerosol delivery devices, we have recognized that opportunities exist for improvement. For instance, the EHD nozzle is to be pointed downwardly in order for each nozzle tip to dispense consistently. However, most users prefer to be upright when using the dispenser. Consequently, the dispensed aerosolized liquid had to be directed through a bend to the exit opening. Momentum of the aerosolized droplets tends to deposit some of the liquid onto the exit opening, reducing the effective dose delivered to the user. In addition, wetting of the interior of the EHD nozzle itself may degrade performance. Most if not all of the liquids dispensed by pulmonary delivery devices to some extent are conductive. Thus, wetting tends to dissipate the desired electric fields within the EHD nozzle, especially should a conduction path be formed between the discharge and reference electrodes. Wetting is mitigated to an extent by procedurally requiring the nozzle to be vertically oriented. Also, the interstitial reference electrodes reduced electrical arcing by greatly reducing a liquid conductive path between the nozzle tips and the reference electrodes. In addition, a current limiting resistor in the voltage producing circuit further controlled arcing. While these measures provided useful handheld dispensers, further enhancements are desirable to further eliminate wetting of the nozzle and to allow use of the dispenser in other orientations.

It is also desirable to have an EHD nozzle that produces a completely electrically neutralized aerosolized liquid. Having some droplets that retain a charge tends to compound wetting of the device or may limit the therapeutic effect (e.g., the mutual repulsion of charged particles may deposit the liquid prior to reaching the fullest extent of the lungs).

One approach that has been suggested is to create a corona of oppositely charged ions that mix with the charged aerosolized liquid droplets prior to leaving an inhaler device as taught by U.S. Pat. No. 4,801,086 to Noakes et al. An air passage is transverse to an aerosolizing chamber, with a positively charged metal capillary tube and a negatively charged discharge electrode on opposite sides of the chamber separated by the air passage. A Taylor Cone at the tube produces a ligament of aerosolized fluid that is attracted toward the discharge electrode. The discharge electrode produces a countering corona of positively charged ions that are directed toward the aerosolized particles, which upon interacting with the negatively charged particles neutralize the negative charge of the aerosolized particles prior to their leaving chamber. To protect the Taylor Cone to a certain extent from attack by the positively charged ions, a shield separates the tube from the air passage and discharge electrode. The shield has an orifice large enough to permit the passage of the aerosolized particles while being sufficiently small to prevent the corona of positively charged ions from passing therethrough to degrade the Taylor Cone formation at the tube.

However, it is believed that this approach to neutralizing the aerosolized liquid has several undesirable limitations. For example, the airflow is transverse to the opposing directions of the aerosolized liquid and ions, creating a turbulence that tends to hamper the neutralizing of the aerosolized liquid prior to exiting the device and tends to wet the interior of the inhaler device. In addition, it is further believed that the neutral shield will tend to be wetted by the aerosolized particles and the volume rate of aerosolized particles will be inconsistent due to the proximity of discharge ions. Thereby the dosage achieved may be inconsistent.

Consequently, a significant need exists for an improved EHD nozzle suitable for use in a portable pulmonary aerosol delivery device.

BRIEF DESCRIPTION OF INVENTION

The invention overcomes the above-noted and other deficiencies of the prior art by providing an improved Electrohydrodynamic (EHD) nozzle that reduces or eliminates wetting of the interior of the nozzle through shielding of discharge electrodes while yet achieving effective neutralization of a dispensed aerosolized liquid. Thereby, a consistent dosage is quickly delivered fully to a patient. Avoiding power dissipation due to wetting makes the EHD nozzle particularly suitable to a handheld pulmonary aerosol inhaler. Furthermore, the high dosage rate with low wetting is achieved while producing an advantageously small particle size suitable for therapeutic liquid dispensers.

In one aspect of the invention, an apparatus and method are described for an improved electrohydrodynamic (EHD) nozzle that includes a shield defining a spray passage having a longitudinal axis. The shield has a downstream opening on the longitudinal axis. An EHD spray nozzle is contained in the spray passage and has a nozzle tip that produces a Taylor Cone toward the downstream opening to aerosolize liquid. Discharge electrodes, which surround the shield, electrically neutralize the aerosolized liquid at the downstream opening while having a reduced likelihood of being wetted by the aerosolized liquid. The EHD nozzle and method increase the consistent and efficient dispensing of therapeutic liquids by reducing or eliminating wetting through shielding of discharge electrodes.

In yet another aspect of the invention, a pulmonary aerosol delivery device is also provided that includes the improved electrohydrodynamic apparatus, enabling improved performance and portable power service life. The delivery device also includes a dispensing system for containing the liquid to be aerosolized and delivering the liquid to the electrohydrodynamic apparatus; a power supply system for providing sufficient voltage to the electrohydrodynamic apparatus to aerosolize the liquid; and a control circuit communicating with the dispensing system. The components are contained within a housing of such size that the housing can be held in a user's hand. With the advantageous reduction of wetting in the electrohydrodynamic device, increased dosage amounts are achievable with additional nozzle tips with the corresponding requirement in voltage levels, without encountering arcing and power dissipation. In addition, with greater achievable power efficiency, the device may achieve longer service life without replacement of the power source (e.g., battery).

In one particular illustrative version, downstream discharge electrodes are substantially shielded by a shield that includes small openings to expose only a tip of each discharge electrode. Thereby, only the tip is subject to attracting and wetting by charged aerosolized liquid. Wetting of the shield is insufficient to form a conduction path from the spray nozzle to the discharge electrode that would draw down the voltage to degrade consistent particle size or produce electrical arcing due in part to the longitudinal length of the discharge electrodes being shielded behind and detached for a substantial length from the shield.

In another particular illustrative version, dissociated discharge electrodes are fully shielded from the spray nozzle and may even be upstream of the plane of the nozzle tip of the spray nozzle. An oppositely charged cloud of ions are ducted annularly downstream to merge with the charged aerosolized liquid, enhancing the flow of aerosolized liquids to the user and neutralizing the aerosolized liquid.

Shielding the discharge electrodes gives additional design options for smaller device size, more economical manufacture, and other advantages. Specifically, the high voltage discharge electrodes present a shock hazard that, if exposed, would require a number of safety steps to prevent injury to the user. With the discharge electrodes recessed between two dielectric walls, the discharge becomes inaccessible to the user which facilitates achieving regulatory approval. For example, an elaborate power supply or circuitry may otherwise be required to limit the amount of electrical current that may be imparted to a user. As another example, an elaborate ducting of the aerosolized liquid may be required to distance exposed discharge electrodes from the user's face or fingers. Such elaborate ducting may not be desirable due to the increased size of the device and loss of aerosolized liquid due to wetting of the ducting.

In yet a further aspect of the invention, some implementations of the EHD nozzle advantageously include: a spray nozzle formed of a dielectric material. An upstream charging electrode imparts an electrical charge to the liquid to be dispensed. Branching channels formed in the spray nozzle provide a controlled pressure drop to a plurality of circumferentially arranged nozzle tips. The controlled pressure drop to each nozzle tip advantageously allows increased dosage production with multiple tips while avoiding undesired variations in the flow rate seen at each nozzle tip, which would affect the achieved particle size.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

DETAILED DESCRIPTION OF THE INVENTION

Figure 1:
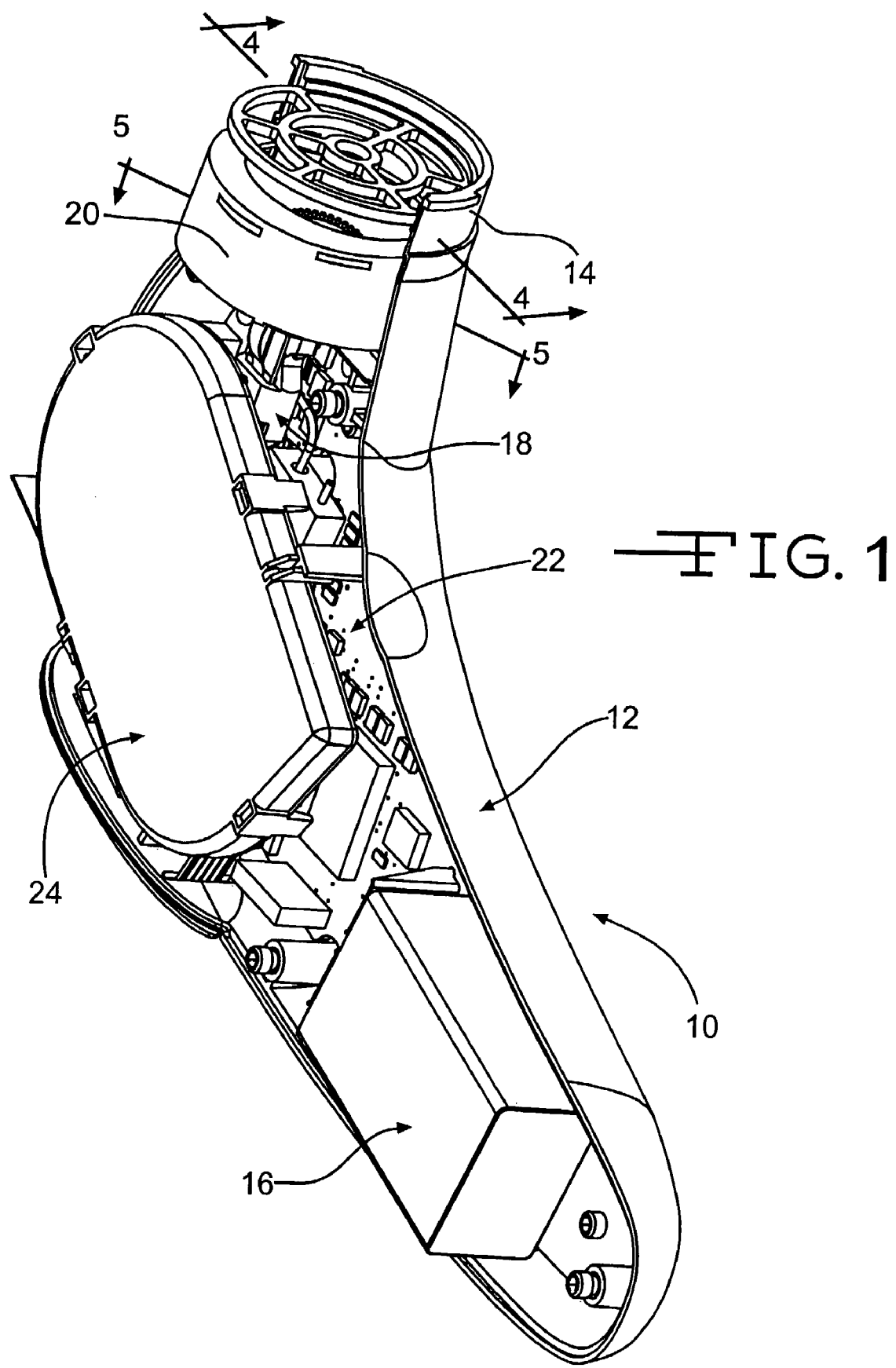
FIG. 1 depicts an improved electrohydrodynamic (EHD) nozzle consistent with the present invention shown installed in a partially disassembled handheld pulmonary delivery device.

Convenience and effectiveness of a hand-held pulmonary delivery device (e.g., inhaler) is enhanced through an improved Electrohydrodynamic (EHD) nozzle. In particular, improvements to EHD nozzles include the equal distribution of fluid to the nozzle tips when the EHD nozzle is aimed at various angles, rather than requiring that the EHD nozzle be aimed downward. The improvements also include several innovations for reducing or eliminating wetting in the EHD nozzle that could degrade voltage and thus particle size or cause arcing between the discharge and reference electronics.

Liquids amenable to aerosolization by electrohydrodynamic spraying generally are characterized by particular electrical and physical properties. Without limiting the scope of the invention, liquids having the following electrical and physical characteristics permit optimum performance by the device and method to generate a clinically relevant dose of respirable particles within a few seconds. The surface tension of the liquid typically is in the range of about 15-50 dynes/cm, preferably about 20-35 dynes/cm, and more preferably about 22-33 dynes/cm. Liquid resistivity typically is greater than about 200 ohm-meters, preferably greater than about 250 ohm-meters, and more preferably greater than about 400 ohm-meters (e.g., 1200 ohm-meters). The relative electrical permittivity typically is less than about 65, preferably less than about 45. Liquid viscosity typically is less than about 100 centipoise, preferably less than about 50 centipoise (e.g., 1 centipoise). Although the above combination of characteristics allows optimum performance, it may be possible to effectively spray liquids with one or more characteristics outside these typical values using the device and method of the invention. For example, certain nozzle configurations may allow effective spraying of less resistive (more conductive) liquids.

Therapeutic agents dissolved in ethanol generally are good candidates for electrohydrodynamic spraying because the ethanol base has a low surface tension and is nonconductive. Ethanol also is an antimicrobial agent, which reduces the growth of microbes within the drug formulation and on the housing surfaces. Other liquids and solvents for therapeutic agents also may be delivered using the device and method of the invention. The liquids may include drugs or solutions or microsuspensions of drugs in compatible solvents.

As described above, the electrohydrodynamic apparatus aerosolizes the liquid by causing the liquid to flow over a region of high electric field strength, which imparts a net electric charge to the liquid. In the present invention, the region of high electric field strength typically is provided by a negatively charged electrode within the spray nozzle. The negative charge tends to remain on the surface of the liquid such that, as the liquid exits the nozzle, the repelling force of the surface charge balances against the surface tension of the liquid, forming a Taylor cone. The electrical force exerted on the liquid surface overcomes the surface tension at the tip of the cone, generating a thin jet of liquid. This jet breaks into droplets of more or less uniform size, which collectively form a cloud.

The device produces aerosolized particles of respirable size. Preferably, the droplets have a diameter of less than or equal to about 6 microns, and more preferably, in the range of about 1-5 microns, for deep lung administration. Because many formulations are intended for deep-lung deposition, at least about 80% of the particles preferably have a diameter of less than or equal to about 5 microns for effective deep lung administration of the therapeutic agent. The aerosolized droplets are substantially the same size and have near zero velocity as they exit the apparatus.

The range of volumes to be delivered is dependent on the specific drug formulation. Typical doses of pulmonary therapeutic agents are in the range of 0.1-100 µL. Ideally, the dose should be delivered to the patient during a single inspiration, although delivery during two or more inspirations may be acceptable under particular conditions. To achieve this, the device generally must be capable of aerosolizing about 0.1-50 µL, and particularly about 10-50 µL, of liquid in about 1.5-2.0 seconds. Delivery efficiency is also a major consideration for the pulmonary delivery device so liquid deposition on the surfaces of the device itself should be minimal. Optimally, 70% or more of the aerosolized volume should be available to the user.

Turning to the Drawings, wherein like numerals represent like components throughout the several figures, FIG. 1 depicts a pulmonary delivery device 10 that includes a housing 12 sized so that it can be held in a user's hand. The housing 12 has an exit opening 14 for directing a dispensed aerosolized liquid to the user's mouth. A silicon face shield (not shown) is attached to the exit opening 14 for re-breathing inhalation by the user from the pulmonary delivery device 10, although it will be appreciated that a mouthpiece may be used in some applications. The housing 12 encloses a portable power supply 16 that provides power to a dispensing system 18, an EHD nozzle assembly 20 of the present invention that receives the liquid from the dispensing system 18 and provides an aerosolized liquid therefrom to the exit opening 14, and a control circuit 22 that actuates the aforementioned components.

The dispensing system 18 holds a supply of the liquid to be aerosolized in a containment vessel 24 that contains and maintains the integrity of the therapeutic liquid. The containment vessel 24 may take the form of a holder for a drug enclosed in single dose units, a plurality of sealed chambers each holding a single dose of the drug, or a vial for enclosing a bulk supply of the drug to be aerosolized. Bulk dosing generally is preferred for economic reasons except for liquids that lack stability in air, such as protein-based therapeutic agents. The containment vessel 24 preferably is physically and chemically compatible with the therapeutic liquid including both solutions and microsuspensions and is liquid- and airtight. The containment vessel 24 may be treated to give it antimicrobial properties to preserve the purity of the liquid contained in the containment vessel 24.

NDD EHD Nozzle. FIGS. 2-5 depict a particular version of the EHD nozzle assembly 20 of FIG. 1, that advantageously provides a non-wettable downstream discharge (NDD) electrode configuration that enhances the consistent performance of the pulmonary delivery device 10. In particular, an NDD EHD nozzle assembly 20a is depicted that includes a plurality of elongated discharge electrodes 26 that are substantially shielded from a spray nozzle 28 by a dielectric discharge shroud 30, mitigating or completing avoiding a wetted path between nozzle tips 32 on the spray nozzle 28 and the elongated discharge electrodes 26. Thereby, performance degradation from arcing and alteration of the electric field strength at the nozzle tips 32 is mitigated or avoided altogether.

Figure 2:
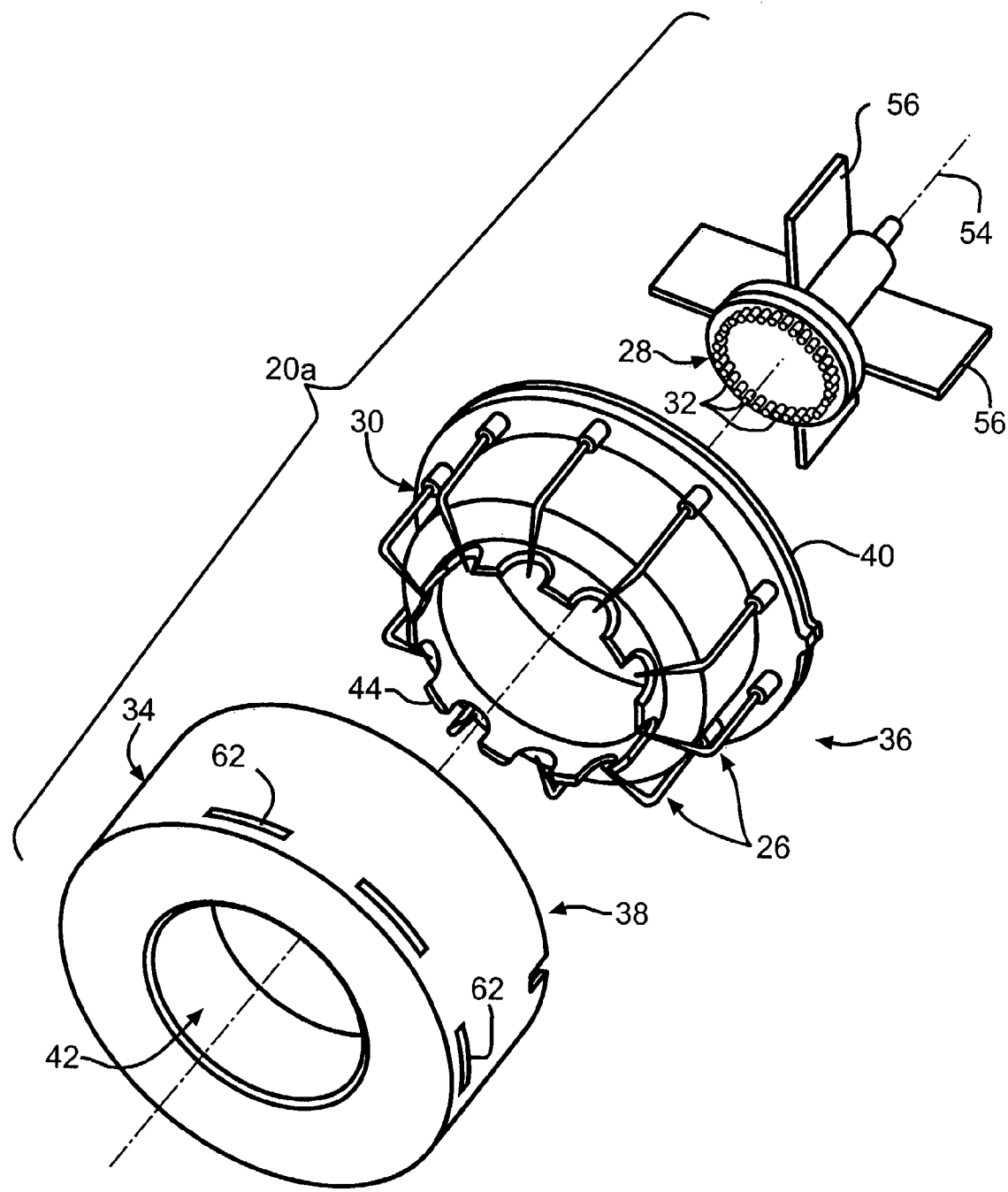
FIG. 2 depicts an exploded view of a multiple tipped, EHD nozzle assembly providing a non-wettable downstream discharge (NDD) nozzle capability for the delivery device of FIG. 1.
Figure 5:
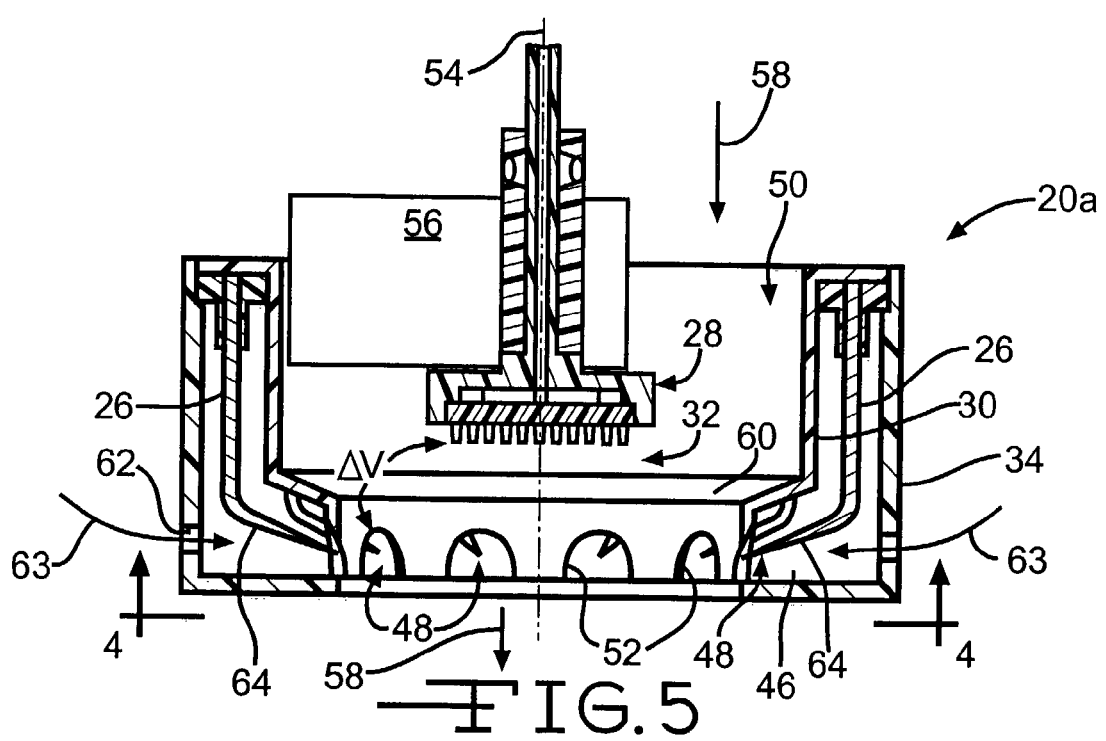
FIG. 5 depicts a cross sectional view taken along line 5-5 of the assembled multi-tipped EHD nozzle assembly of FIG. 1.
Figure 6:
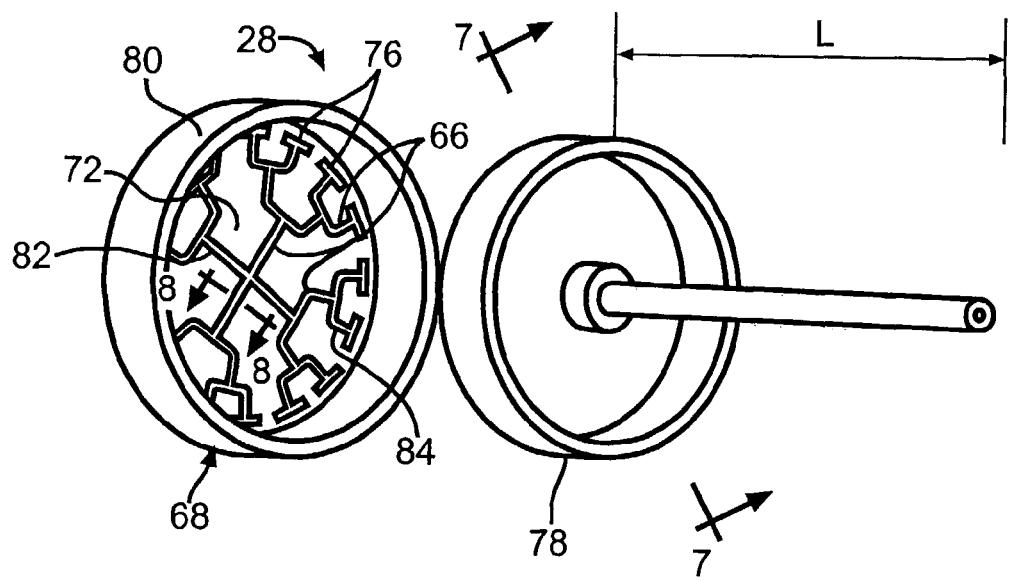
FIG. 6 depicts an exploded pictorial view of a spray nozzle, including fluidic distribution passages and purely dielectric spray sites, of the EHD nozzle assembly of FIG. 1.
Figure 7:
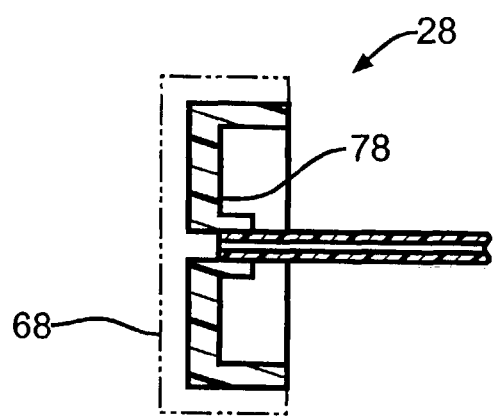
FIG. 7 depicts a sectional view taken along line 7-7 of the spray nozzle of FIG. 6.
Figure 8:
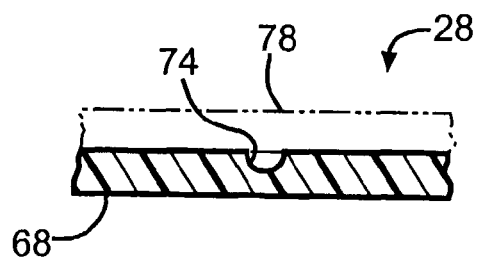
FIG. 8 depicts a sectional view taken along line 8-8 of the spray nozzle of FIG. 6.

With particular reference to FIG. 2, an open cylinder-shaped outer shell or cover 34 receives a discharge assembly 36 that includes the dielectric discharge shroud 30 and the elongated discharge electrodes 26. A rear opening 38 of the cover 34 slidingly receives a rear annular flange 40 of the dielectric discharge shroud 30. A reduced diameter front opening 42 of the cover 34 engages a forward-facing scalloped ring 44 of the dielectric discharge shroud 30. With particular reference to FIG. 5, a discharge electrode chamber 46 is formed between the dielectric discharge shroud 30 and cover 34 thereby shielding the elongated discharge electrodes 26, with the exception of each discharge electrode tip 48 of each elongated discharge electrode 26 that is exposed to a spray passage 50, which is longitudinally defined inside of the dielectric discharge shroud 30, through a respective discharge electrode opening 52 formed by the forward facing scalloped ring 44 and the reduced diameter front opening 42. Each elongated discharge electrode 26 begins with a rearward portion that is longitudinal aligned with a longitudinal centerline 54 of the NDD EHD nozzle assembly 20a, transitioning to an obliquely inwardly angled portion 64 terminating in the discharge electrode tip 48.

In addition to reducing wetting, it will be appreciated that discharge electrode openings 52 of sufficiently small size reduce the likelihood of contact with the user, thereby reducing a shock hazard. Thus, the NDD EHD nozzle assembly 20a may advantageously be used in close proximity to the user's mouth. Moreover, a great variety of power supplies and power storage devices may be used in conjunction with the NDD EHD nozzle assembly 20a.

The spray nozzle 28 is centered on the longitudinal centerline 54 within the spray passage 50 by a plurality of positioning plates 56 that are longitudinally aligned and respectively radially spaced to contact the interior of the dielectric discharge shroud 30.

Figure 3:
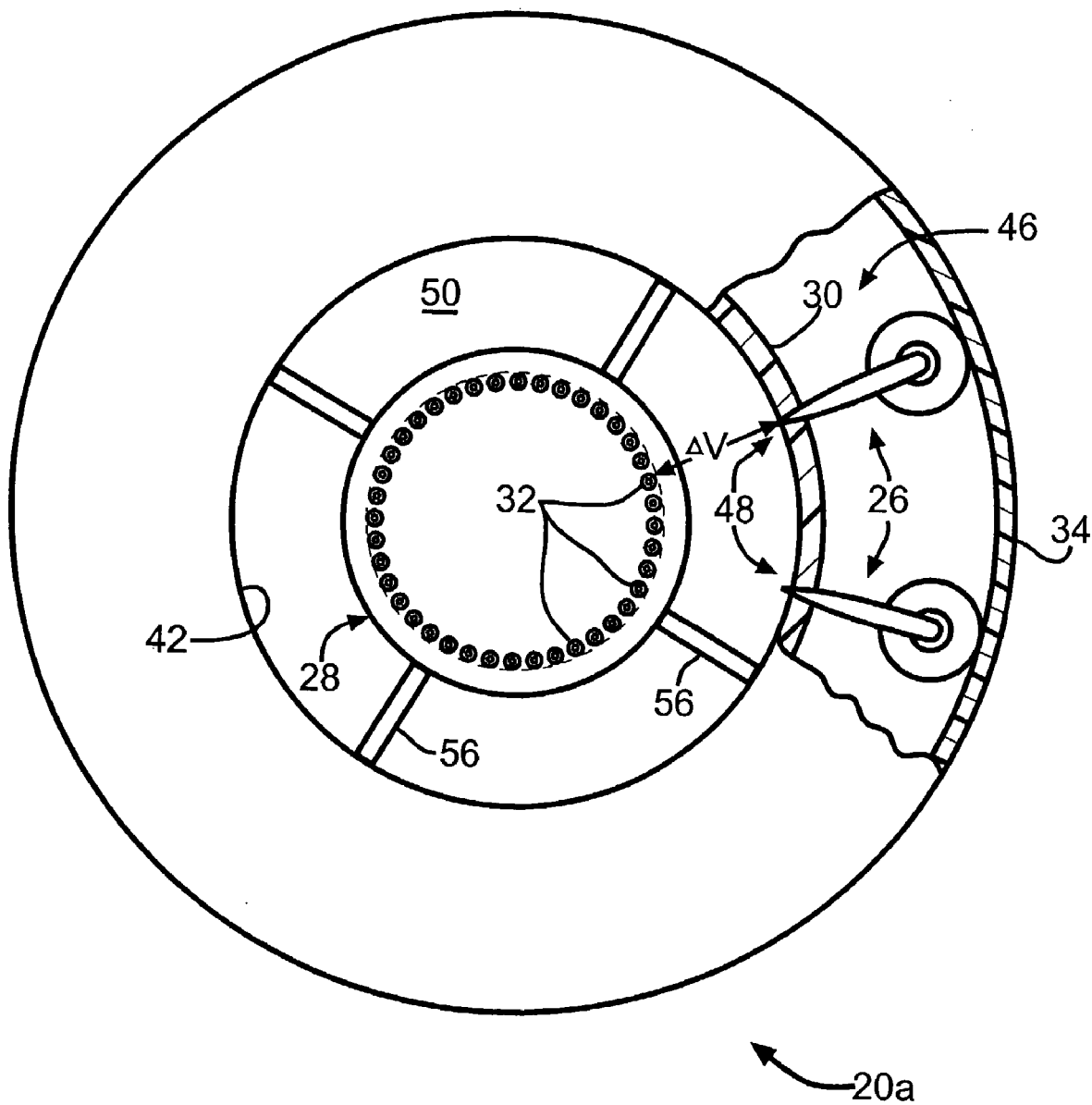
FIG. 3 depicts a front elevational view of the assembled multi-tipped EHD nozzle assembly of FIG. 1 with a portion cut away to view two of a plurality of non-wettable downstream discharge electrodes.

As depicted in FIGS. 3 and 5, the nozzle tips 32 (or spray sites) are given a voltage differential ΔV with respect to the elongated discharge electrodes 26. In an illustrative version, a symmetrical power source is used to provide a −5 kV at the nozzle tips 32 and a +5 kV at the elongated discharge electrodes 26. However, it will be appreciated by those skilled in the art having the benefit of the present disclosure that a voltage difference may be used having an opposite polarity or a different magnitude. For example, the nozzle tips 32 may be at ground potential and the discharge electrodes may be at +10 kV, thereby an exposed nozzle tip 32 does not present a shock hazard to a user. The nozzle tips 32 produce an EHD spray under the influence of the resultant electrical field that causes the Taylor cone at one or more nozzle tips 32 to eject an aerosol jet.

Figure 4:
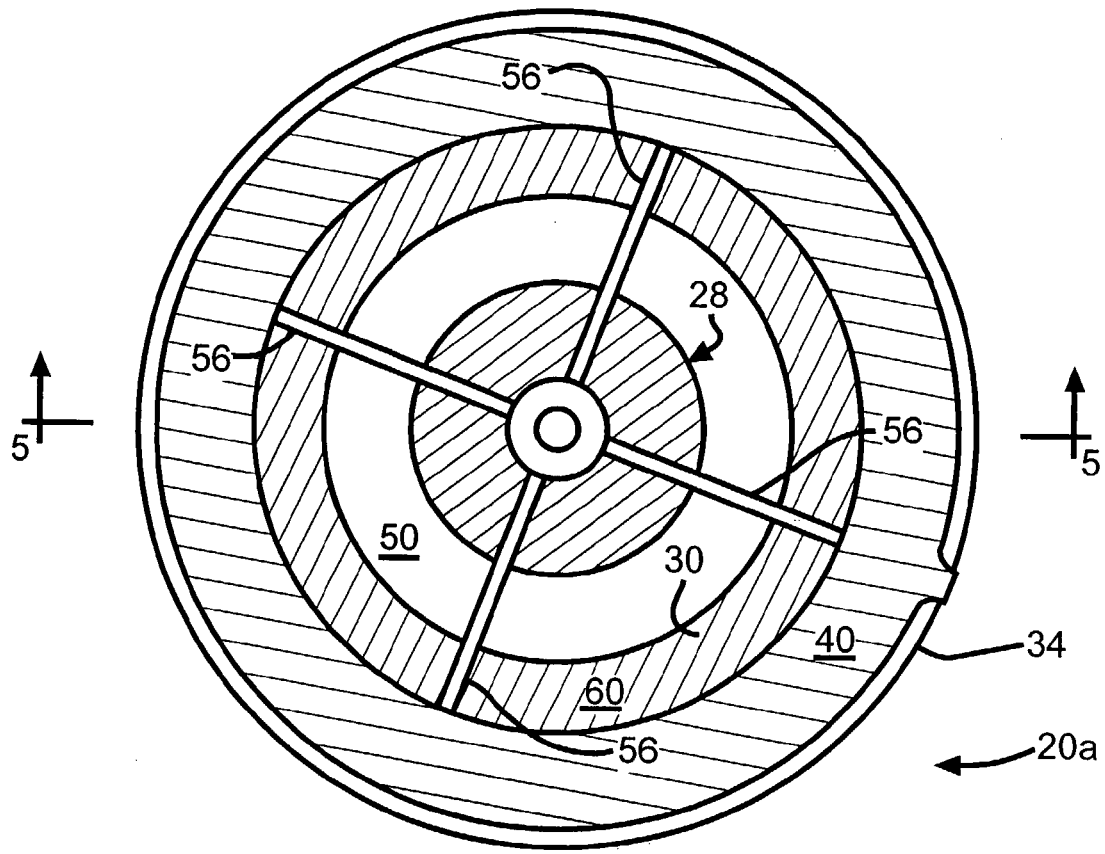
FIG. 4 depicts a rear elevational view, looking forward, taken along line 4-4 of the assembled multi-tipped EHD nozzle assembly of FIG. 1.

The spray passage 50 passes through the NDD EHD nozzle assembly 20a as viewed from the front and rear respectively in FIGS. 3 and 4, allowing the user to inhale air through the NDD EHD nozzle assembly 20a, as depicted at arrow 58, or exhale in an opposite direction. During inhalation with the nozzle tips 32 producing an aerosolized liquid, the air flow through the spray passage 50 and around the spray nozzle 28 helps to minimize wetting of the forward, interior surfaces of the dielectric discharge shroud 30. In particular, a constriction 60 in the spray passage 50 inwardly deflects airflow overcoming the mutual repulsion of the charged droplets that are expelled from the nozzle tips 32.

An additional airflow path is provided from a plurality of vents 62 that are radially spaced about the exterior of the cover 34 near the front. As depicted in FIG. 5, vent air flow during inhalation is as depicted at arrows 63 whereby air enters through the vents 62, passes around an inwardly and obliquely inwardly angled portion 64 of the elongated discharge electrodes 26 and through the discharge electrode openings 52 into air flow of inhaled air 58 of the spray passage 50. Air passing near the discharge electrode tips 48 is ionized in an opposite sense to the aerosolized liquid and is presented in front of the aerosolized liquid, thereby further enhancing the flow of aerosolized liquid out of the reduced diameter front opening 42 by electrical attraction. The convergence also electrically neutralizes the aerosolized liquid, as is generally preferred, to fully reach the patient's lungs. The self-aspirating feature of the vents 62 enhances performance of the elongated discharge electrodes 26 by enabling creation of an ion wind.

In addition to directing airflow to reduce wetting, the dielectric discharge shroud 30 is advantageously formed from a dielectric material so that an accumulated charge from droplets of the charged aerosolized liquid will tend to repulse the attachment of additional droplets. Furthermore, as best viewed in FIG. 5, it is believed that wetting is unlikely to occur along the full path between a nozzle tip 32, across a positioning plate 56, and along the interior of the dielectric discharge shroud 30. Thus, wetting is unlikely to thereby facilitate arcing across a discharge electrode opening 52 to a discharge electrode tip 48. The entire length of this wetting path is less likely to be wetted than in conventional EHD nozzles. Moreover, proper sizing of the discharge electrode openings 52 with respect to the voltage used and conductivity of the therapeutic liquid may further reduce the likelihood of arcing.

With increased resistance to wetting, simpler controls may be employed, with resulting decreases in unit costs and increased unit reliability. For instance, inhalation sensors are often used to sense an intake of breath so that dispensing is prevented during exhalations. In these generally known devices, dispensing during exhalation would tend to deposit a quantity of the therapeutic liquid onto the interior of the EHD nozzle. With the advantages of this simplified control, however, the present NDD EHD nozzle assembly **20*a*** may be used in new ways, such as in a rebreathing operation wherein the patient may inhale and exhale through the device. Although the patient would be instructed to initiate dispensing by depressing a button or other control during inhalation, inadvertent activation during exhalation would not impair operation. It will be appreciated that inhalation sensors may be used in some applications, however.

Fluidic Distribution Passages in the Spray Nozzle. FIGS. 6-9 depict in greater detail an illustrative molded spray nozzle 28 for use in the EHD nozzle 20 described above. With particular reference to FIGS. 6-8, the spray nozzle 28 is shown as advantageously including fluidic distribution passages 66 that enable the efficient and effective use of NDD EHD nozzle assembly **20*a*** at orientations other than vertically downward.

With reference to FIGS. 6-9 , the spray nozzle 28 comprises a face plate 68 having Taylor Cone forming dielectric nozzle tips 70 that are equally positioned about the circumference of face plate 68, as best illustrated in FIG. 9. On a rearward facing surface 72 of the face plate 68 is a family of grooved channels 74 extending from the center of face plate 68 to a respective passthrough orifice 76 to each of the dielectric nozzle tips 70. A backing plate 78 is sealingly (e.g., press fit, bonded, welded, etc.) received within a rearwardly projecting collar 80 attached to the face plate 68, completing the spray nozzle 28. The sprue like grooved channels 74 emanate and branch from the center of rearward facing surface 72 outward to each of the dielectric nozzle tips 70. In operation, four main sprues 82, radiating from the center of the rearward facing surface 72 of face plate 68, receive fluid from a main supply 83 and distribute fluid to branching sprues 84 thereby supplying fluid to each of the dielectric nozzle tips 70. In particular, the approach of the branching pattern of grooved channels 74 creates fluidic paths from the center of face plate 68 to each dielectric nozzle tip 70 so that the hydrodynamic affects of pressure drop and fluid flow rate are similar for all dielectric nozzle tips 70 being supplied, even at varying orientations. Thus each dielectric nozzle tip 70 should theoretically receive fluid at similar flow rate and pressure and thereby dispense aerosol droplets at a comparable particle diameter and volume rate.

It will be appreciated that in some applications the grooved channels 74 may create a greater, although consistent, pressure drop, than used in generally known dispensers thereby requiring an increased pump pressure requirement to dispense and distribute liquid to the dielectric nozzle tips 70. The increased pressure drop is believed to advantageously maintain a high fluid velocity that renders less significant the relative height between dielectric nozzle tips 70 and any inconsistent dispensing volume and particle size.

Although the spray nozzle 28 described above illustrates sprue like grooved channels 74 that are symmetrically positioned about the centerline of the spray nozzle 28, it is within the teaching of the present invention to arrange the sprue like grooved channels 74 in any suitable pattern that may not necessarily be symmetrical. For example if a non-uniform fluid flow rate were desired from the dielectric nozzle tips 70, the grooved channels 74 might take on any number of patterns wherein the sprues are not necessarily symmetrical, of equal length, and/or of equal channel diameter. Furthermore, selection of a desired pressure drop may be achieved with less branching and less turns in each grooved channel 74. For example, a radial spoke arrangement may be used without any turns and with all of the branching achieved at a central liquid passage.

Departing from a circular and radially symmetrical arrangement of grooved channels 74 may be particularly appropriate when the nozzle tips 70 are arrayed in a non-circular arrangement. For instance, an oval or rectangular face plate may advantageously allow a thinner device to be achieved that is more easily carried in a pocket. The arrangements of nozzle tips may thus be arranged along the periphery of such a face plate. Alternatively, rows of nozzle tips may be arranged along the width of the face plate, perhaps with a staggered pattern, similar to the stars on the field of the U.S. Flag, so that repulsion from nearby nozzle tips are accounted for and a desirable spray pattern achieved. The fluid passages to these non-circularly arrayed nozzle tips may advantageously be varied from a radially symmetrical pattern so that each nozzle tip receives a nearly equivalent flow rate as other nozzle tips.

Purely Dielectric Spray Sites. An alternative or additional feature is depicted in FIG. 9 of a spray nozzle 28 formed purely from dielectric material with the dispensed liquid carrying an electrical charge injected prior to entering the spray nozzle 28. The purely dielectric spray nozzle 28 has less of a tendency for wicking of liquid at its dielectric nozzle tips 70. Wicking losses, which may occur even when the electric field is off, are advantageously controlled to allow both sustained operation of the NDD EHD nozzle assembly 20a and thereby delivery of the expected dose of the therapeutic liquid to a user. If uncontrolled, wicking may result in submersion of the dielectric nozzle tips 70 and cessation of spray activity. Wicking losses are thought to result from the low surface tensions of the liquid formulations (as low as about 15 dynes/cm). To control wicking, the outer diameter of the dielectric nozzle tips 70 or other surfaces of interest may be formed from a low surface energy material, thereby eliminating the need for a secondary manufacturing operation to add a hydrophobic coating.

FIG. 10 schematically illustrates a single EHD nozzle assembly 86 comprising a purely dielectric tube 88, a tip 90 and a high voltage metallic, fluid supply assembly 92. Dielectric tube 88 and tip 90 comprise a purely dielectric, non-conducting, material such as, but not limited to, polycarbonate, Acetal, Teflon, etc. High voltage fluid supply assembly 92 includes a suitable metallic discharge tube 94 through which an electrically conductive liquid, supplied by a suitable pump 96 ("P"), flows from high voltage supply assembly 92 into and through dielectric tube 88 exiting at tip 90. Tip 90 may comprise any exit configuration suitable for Taylor Cone formation. As the electrically conductive liquid passes through high voltage supply assembly 92 the fluid becomes negatively charged by virtue of the supply assembly 92 being negatively charged by a DC power source 98.

In a laboratory test apparatus as depicted in FIG. 10, the physical dimensions of length "D1" of dielectric tube 88 and height "D2" from a positively charged ground plane 100 were 25 and 22 centimeters respectively and the metallic discharge tube 94 was 12 gauge stainless steel. As the negatively charged fluid exits tip 90, a Taylor cone 102 forms and becomes attached to the exit end of the tip 90 thereby producing a mist of negatively charged liquid particles 104. The negatively charged liquid particles 104, forming a monodispersed electrospray 106, are attracted to and impinge upon the positively charged ground plane 100. Initial laboratory tests resulted in a monodispersed electrospray liquid particles 104 having a mean particle size (by volume) as low as 1.56 microns at a fluid flow rate of 0.5 microliters per second. When the fluid flow rate had been increased to 2.0 microliters per second, the mean particle size had increased to 3.6 microns.

Figure 10:
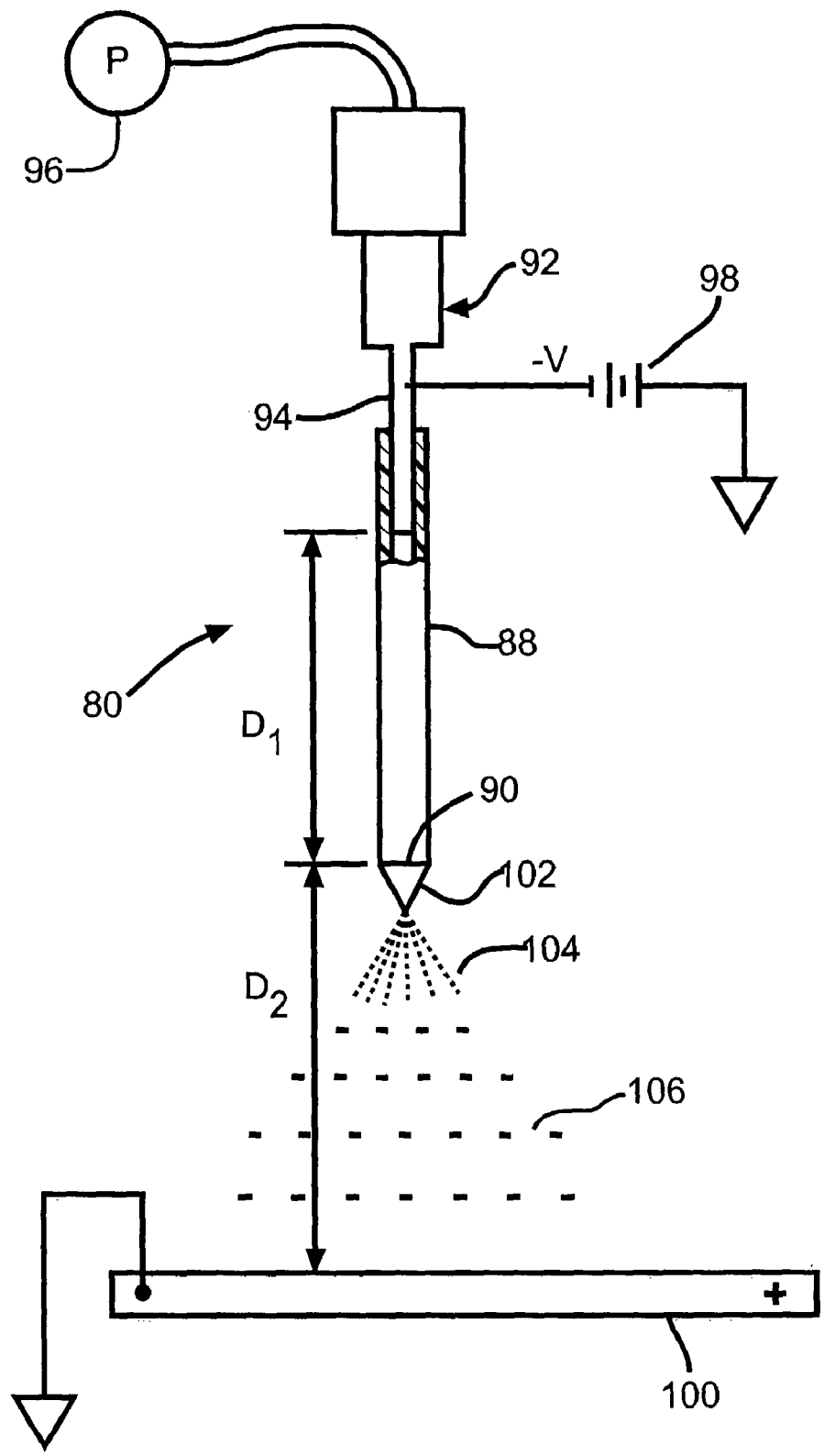
FIG. 10 depicts a schematical view of a single electrohydrodynamic (EHD) spray nozzle formed from purely dielectric material.

Another laboratory test employing similar apparatus as illustrated in FIG. 10 using an all metal, stainless steel ball tip (not shown), tested with a similar ground plane relationship as illustrated in FIG. 10 and operating at a fluid flow rate of 0.25 microliters per second, provided a monodispersed electrospray having a mean particle size (by volume) of 5.59 microns, significantly larger than that obtained using the dielectric tip. Thus, the higher surface energy of stainless steel resulted in larger particle diameter.

It will be appreciated that a positively charged liquid impinging upon a negative charged ground plane 100 would achieve similar results. It is also to be appreciated that, although the test apparatus described above employed an electrically charged discharge tube 94 to negatively charge and introduce the electrically conductive fluid into dielectric tube 88, other alternative methods of electrically charging the fluid, as it passes into and/or through dielectric tube 88, may be used. For example an electrode may be placed within the dielectric tube 88, anywhere along its length, whereby the electrode, in contact with the passing fluid, thereby charges the fluid prior to the fluid exiting tip 90. Furthermore, the dielectric tube 88 itself may be replaced with a metallic structure that charges the liquid, relying upon the purely dielectric tip 90 itself to provide the advantages of a dielectric material. As another example, the nozzle tip may be at ground potential with the Taylor cone formed by an electric field formed by a charged discharge electrode or an ion cloud created by the charged discharge electrode.

The purely dielectric spray nozzle 28 is effective for electrospraying while advantageously reducing wicking and may be economically fabricated. However, in some applications, the economical fabrication of a molded spray nozzle from a purely dielectric material is desirable; however, a conductive or semi-conductive nozzle tip is desired to reduce transitory effects and to thereby reach the steady state volume rates and particle size. For instance, carbon or other conductive particles such as metal (e.g., silver, gold) may be loaded into the dielectric material prior to molding or be applied to the exterior surface of the spray nozzle after molding. Alternatively, a thin layer of metal such as silver or gold may be deposited upon the spray nozzle, such as through vacuum sputtering or a similar process.

Figure 9:
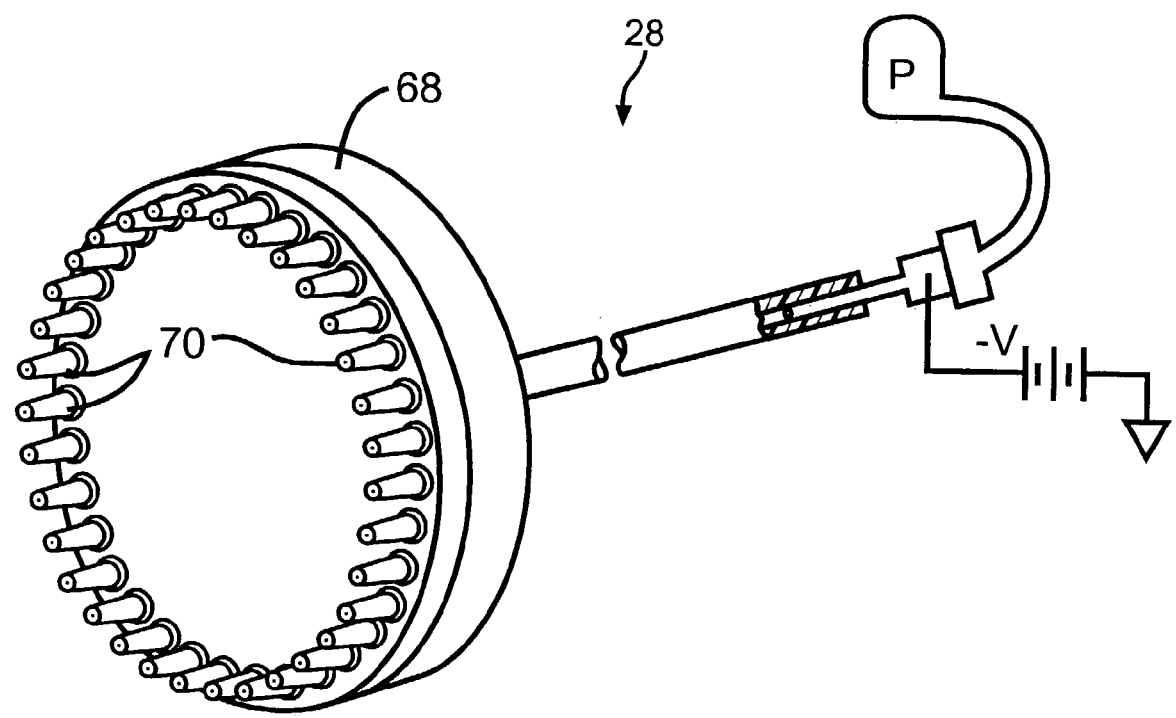
FIG. 9 depicts a front pictorial view of the spray nozzle of FIG. 6.

Returning to FIG. 9, the spray nozzle 28 as illustrated having thirty four dielectric nozzle tips 70 has been bench tested in the horizontal position with respect to its longitudinal axis at flow rates ranging from 5 to 16 micro-liters per second without loss of the Taylor Cones formed at each tip. Atomized particle sizes were on the order of 1.4 to 1.5 microns. The physical dimensions of the test nozzle assembly were: Diameter (D)=0.55 inches; Diameter of tip circle (d)=0.049 inches; Tip OD=0.020 inches; Tip ID=0.0043 inches; and Length of supply tube (58)=0.875 inches.

Figure 11:
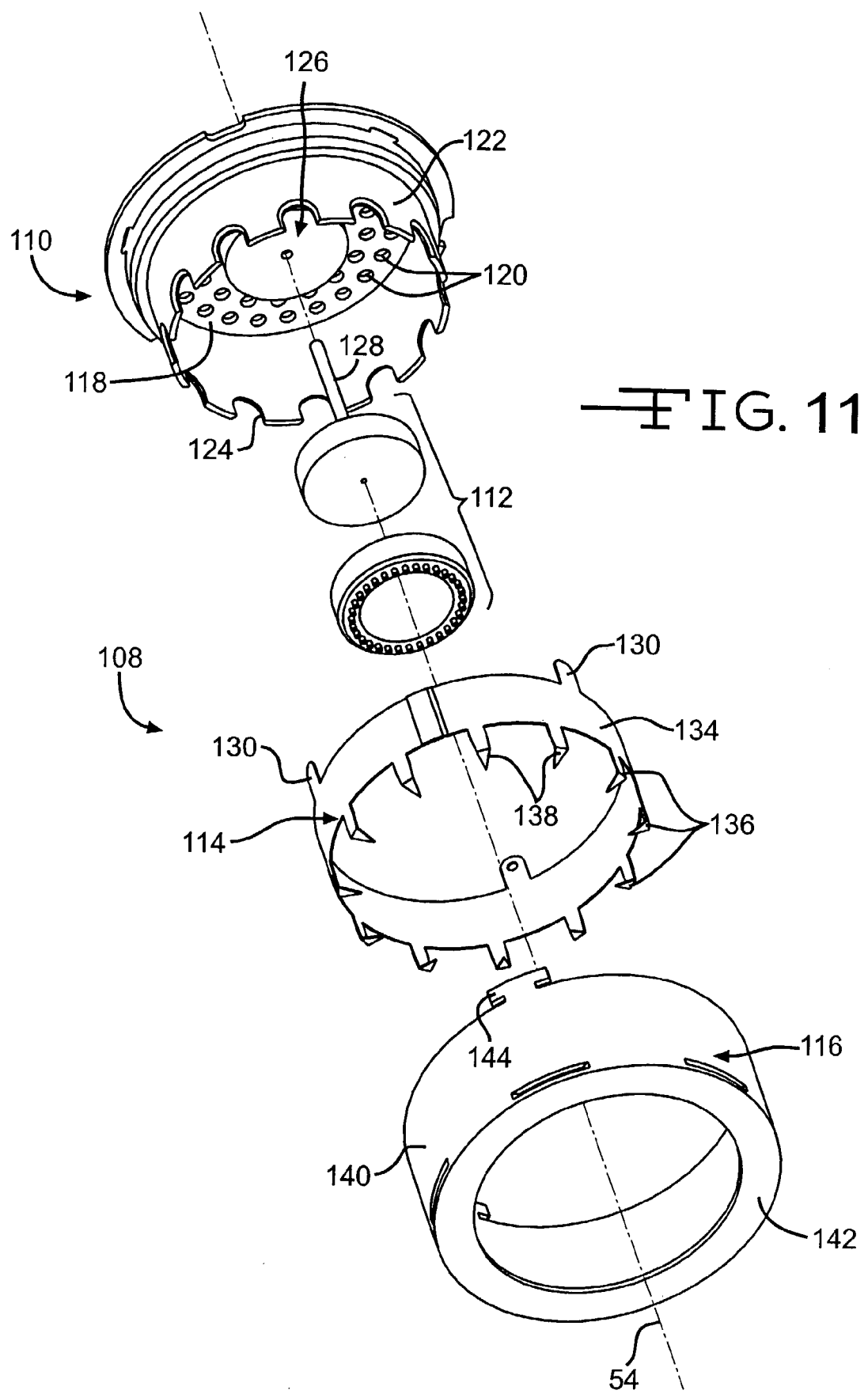
FIG. 11 depicts an exploded pictorial view of an alternate version of the multiple-tip EHD nozzle assembly for the delivery device shown in FIG. 1.

Snap-fit NDD EHD Nozzle. FIGS. 11-15 depict another version of an NDD EHD Nozzle assembly 108 that advantageously includes manufacturability features including simplified discharge electrodes and a snap-fit assembly. As illustrated in FIG. 11, the snap-fit NDD EHD nozzle assembly 108 comprises a unitary, dielectric, cylindrical base structure 110; a spray nozzle 112; a unitary, cylindrical, multi-electrode discharge band 114; and a unitary dielectric, cylindrical cover 116. All of the aforementioned elements are depicted as coaxial about a longitudinal centerline 54.

The unitary, dielectric, cylindrical base structure 110 comprises a circular back wall 118 having a multiplicity of apertures 120 to permit the flow of air therethrough during inhalation by the user. Extending axially forward from the circular back wall 118 is a cylindrical collar 122 having a multiplicity of open ended, U shaped openings 124 circumscribing the distal periphery of the cylindrical collar 122. Although U-shaped openings 124 are illustrated as being open-ended, they may also have closed ends and be other than U-shaped.

Figure 14:
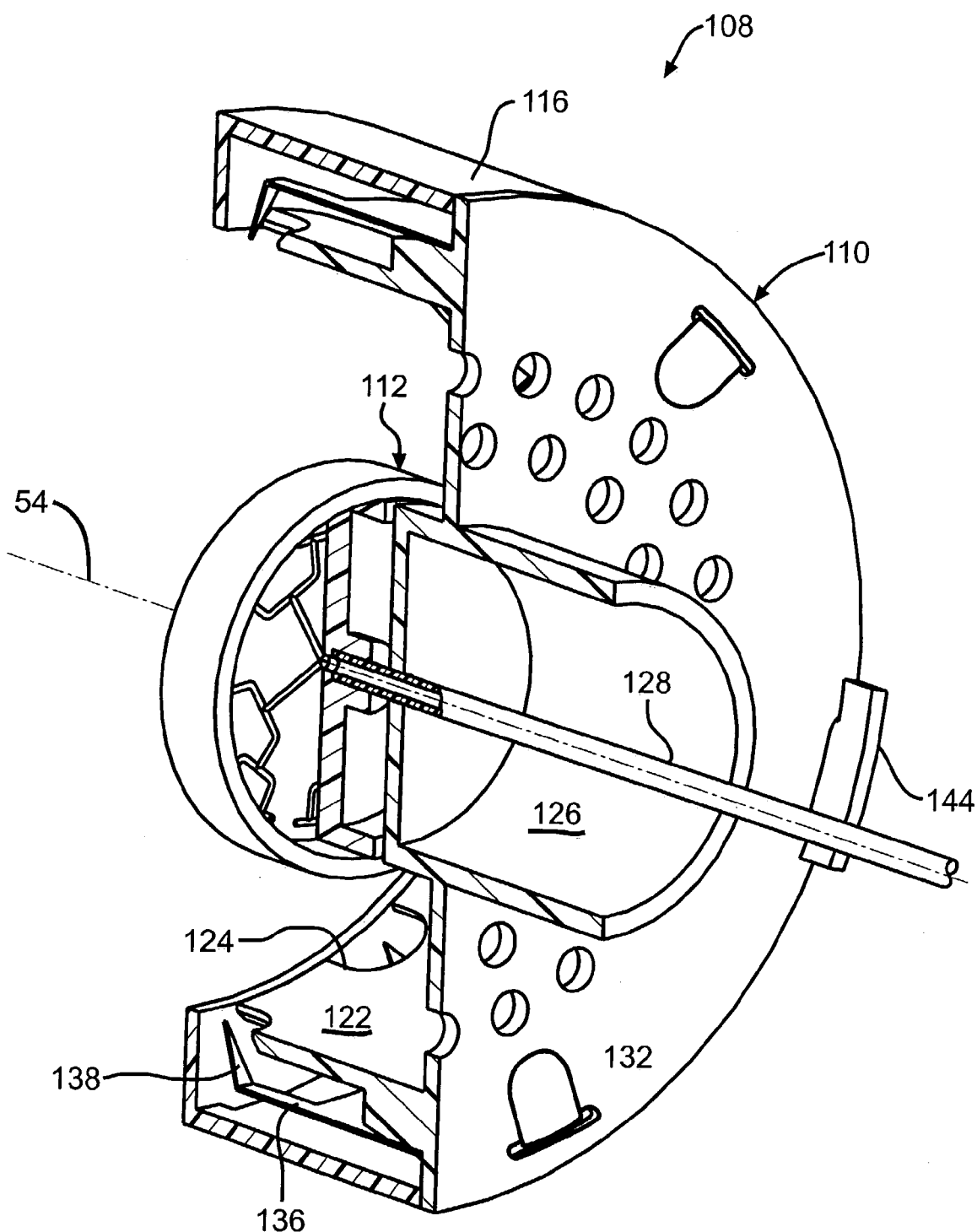
FIG. 14 depicts a rear three-quarters sectioned pictorial view of the EHD nozzle assembly of FIG. 11.
Figure 15:
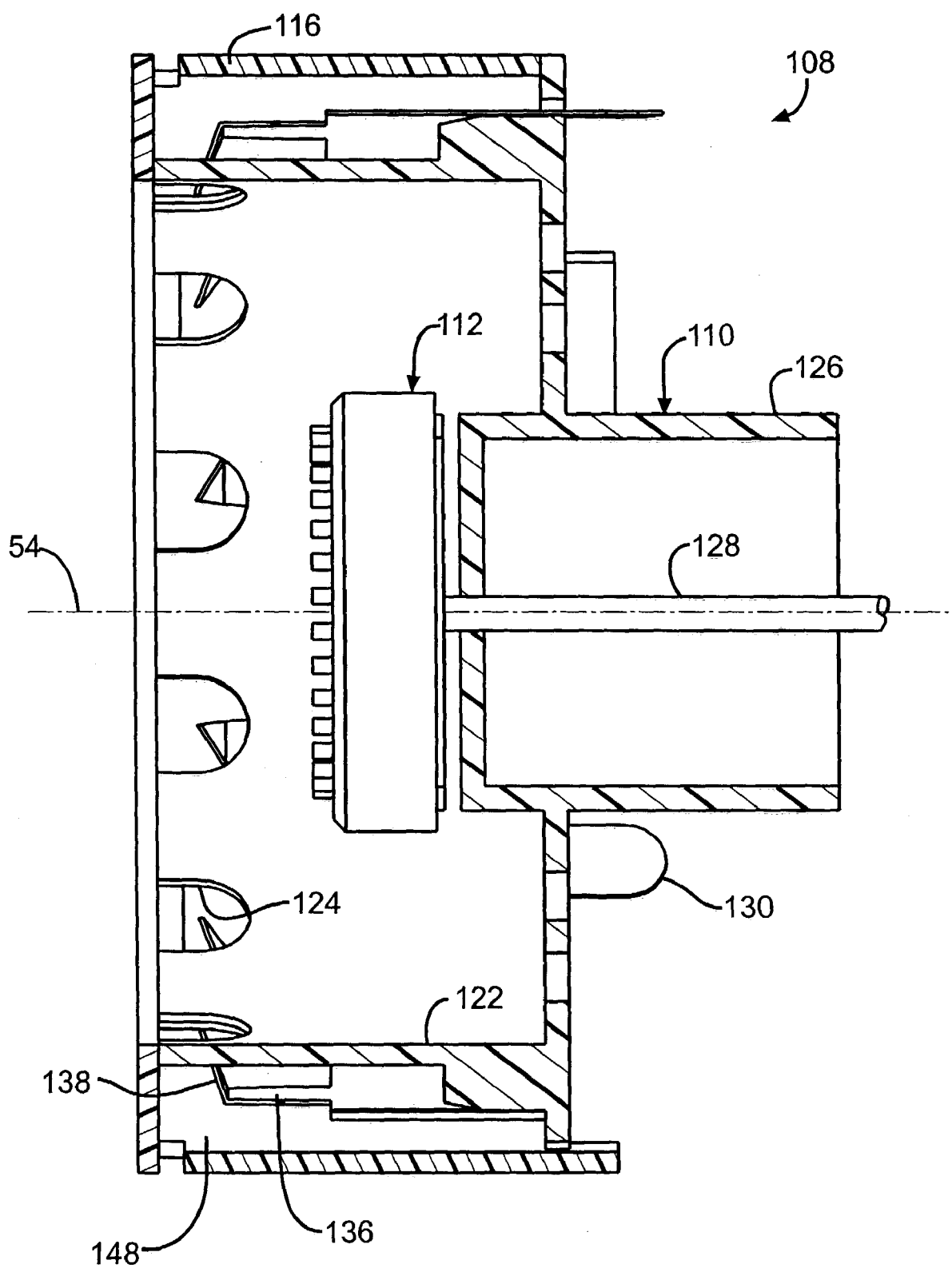
FIG. 15 depicts a sectioned elevational view taken along the centerline of the EHD nozzle assembly of FIG. 11.
Figure 16:
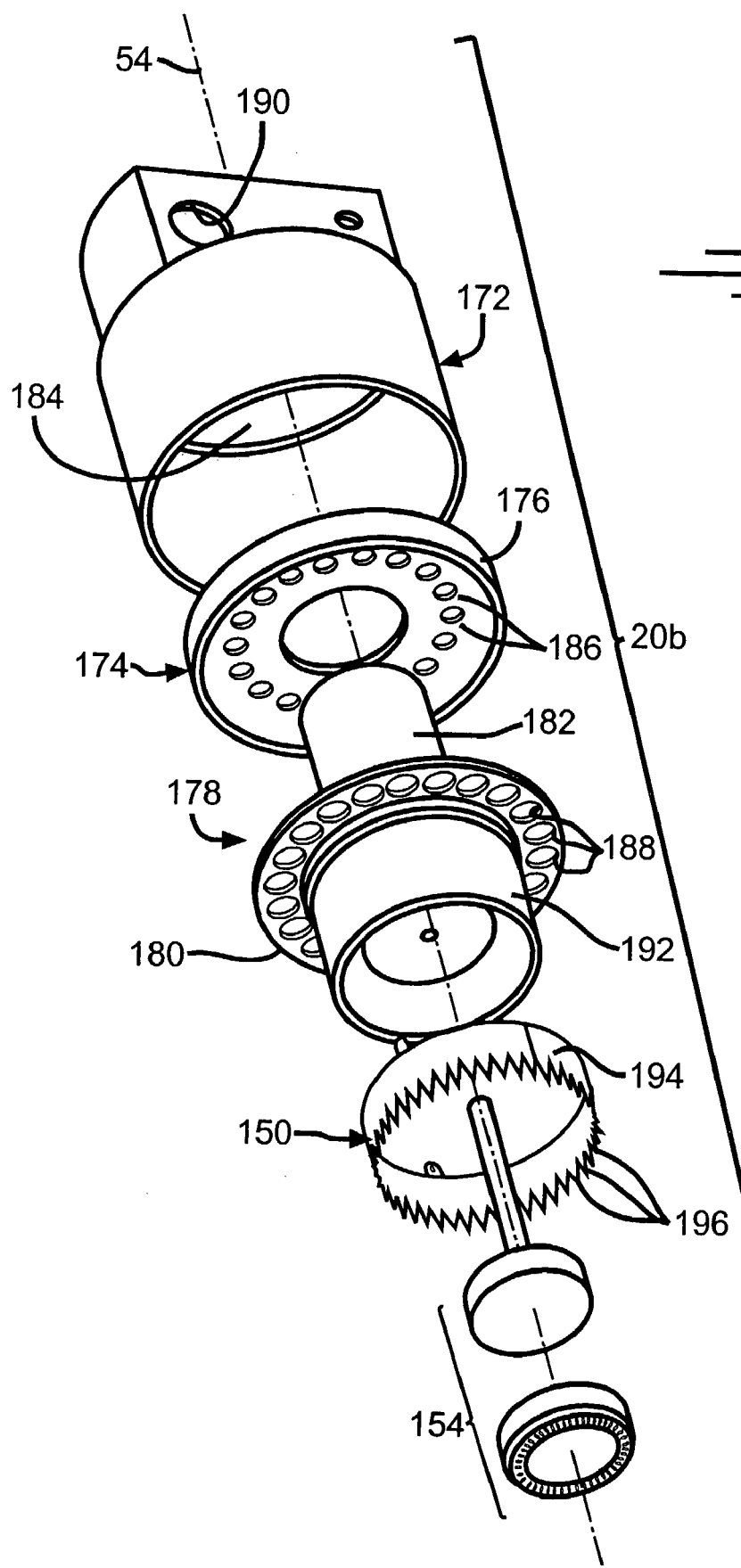
FIG. 16 depicts an exploded pictorial illustrating the major components of a further alternate version of the multiple-tip EHD nozzle assembly utilizing a Dissociated Downstream Discharge (DDS) electrode for the delivery device shown in FIG. 1.
Figure 17:
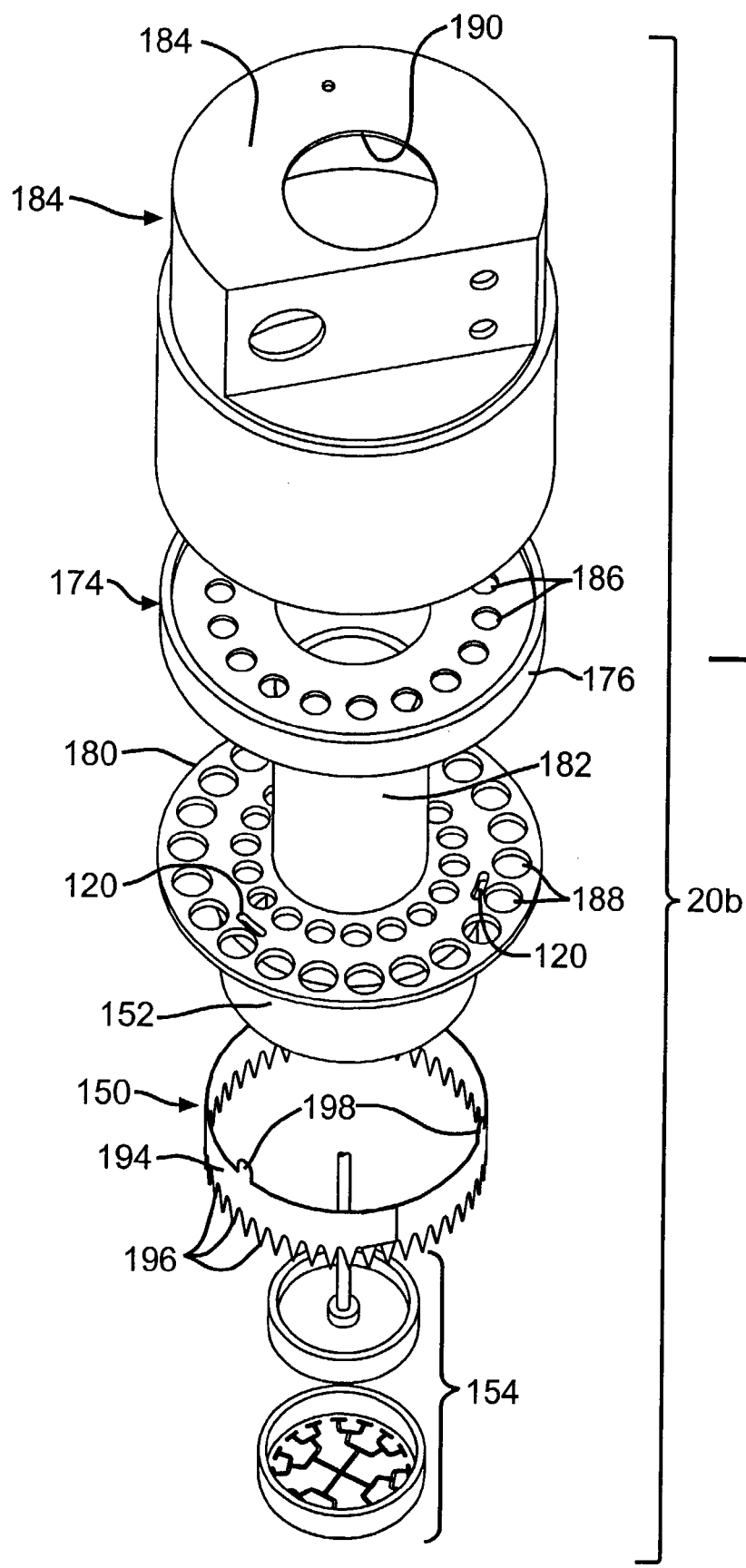
FIG. 17 depicts a reversed exploded pictorial illustrating the DDS multiple-tip EHD nozzle assembly shown in FIG. 16.

Integral with cylindrical base structure 110 and extending through the circular back wall 118 is a closed ended tube 126 upon which spray nozzle 112 is attached via a fluid supply tube 128 that extends rearward from the spray nozzle 112 and through the closed ended tube 126 as best illustrated in FIGS. 14-15.

Mounted upon and circumscribing the cylindrical collar 122 is the stainless steel discharge band 114 that includes a multiplicity of integral metal tangs 130 that are received within open slots 132 of the circular back wall 118 and bent over, as illustrated in FIG. 14, thereby securing multi-electrode discharge band 114 to the base structure 110. The multi-electrode discharge band 114 also comprises a cylindrical base strap 134 having a multiplicity of electrodes 136 extending axially forward from the cylindrical base strap 134 as best illustrated in FIG. 11. Electrodes 136 are provided with sharply pointed ends 138 that are bent obliquely toward the longitudinal axis and centered within openings 124 of the cylindrical collar 122. When the multi-electrode discharge band 114 is positively charged, a field of positive ions is directed from each electrode 136 toward the longitudinal axis downstream of the spray nozzle 112, thereby directing the flow out of the pulmonary delivery device 10 and increasing the mass transfer achieved.

Figure 12:
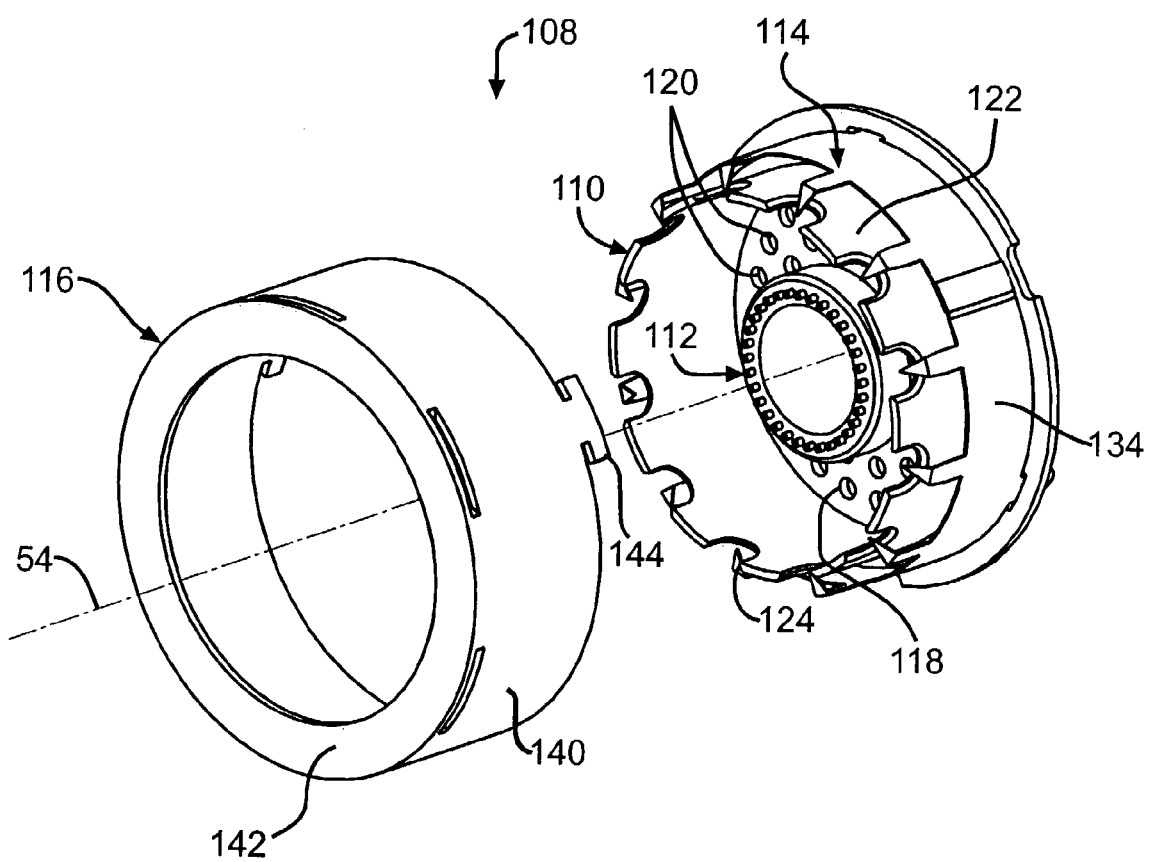
FIG. 12 depicts a partially exploded pictorial view of the multiple-tip EHD nozzle assembly FIG. 11
Figure 13:
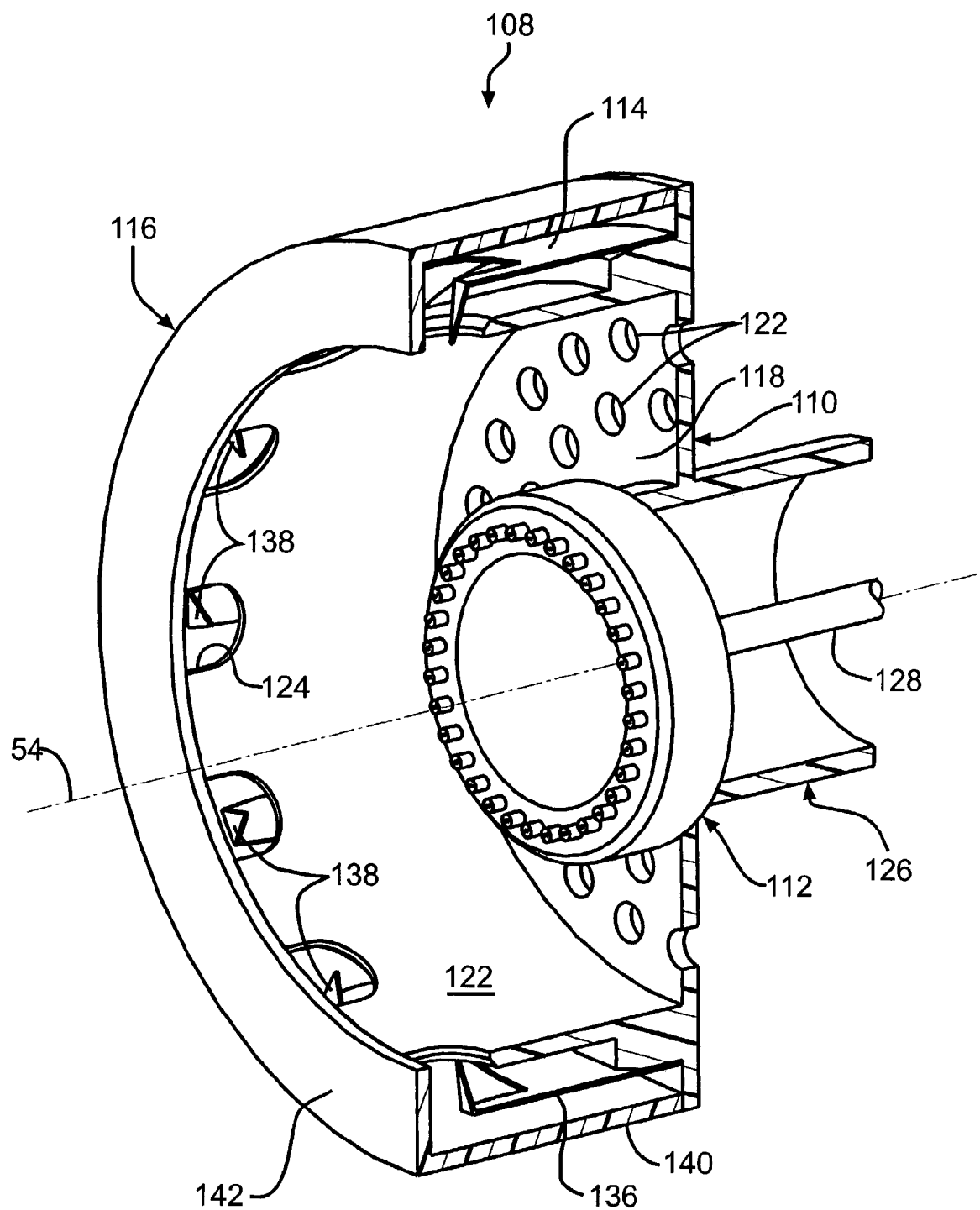
FIG. 13 depicts a three-quarters front sectioned, pictorial view, of the EHD nozzle assembly of FIG. 11.

The protective cover 116 comprising a cylindrical shell 140 having a radially inward rim 142 that surrounds the subassembly of parts and attaches to base structure 110 by three or more tabs 144 that are received within open slots 146 of the base structural 110 as seen in FIG. 12. Cover 116, cylindrical collar 122 and radially inward rim 142 cooperate to form an enclosed annular discharge electrode chamber 148 having a multiplicity of circumscribing openings 124 within which a pointed end of a respective electrode 136 is centered as best illustrated in FIG. 15.

Dissociated Discharge Shroud (DDS) Turbine EHS Nozzle. FIGS. 16-19 depict another alternative EHD nozzle assembly 20b that includes a disassociated, upstream discharge electrode 150. Being upstream of and shielded by a dissociated discharge shroud 152, the discharge electrode band 150 is protected from wetting from a spray nozzle 154. Moreover, a corona of ions oppositely charged to that of an aerosolized liquid from the spray nozzle 154 are dispensed in a forward annular fashion around the aerosolized liquid, creating an advantageous airflow pattern for neutralizing the aerosolized liquid while not wetting the interior of the DDS EHD nozzle assembly 20b.

The sharply pointed dissociated, upstream discharge electrode 150 is maintained at a relatively high positive electrical charge whereby air surrounding the dissociated, upstream discharge electrode 150 is electrically broken down to form a cloud of positively charged ions 156. At standard temperature and pressure, it is generally recognized that air will ionize when subjected to an electrical field strength of 30,000 V/cm. The cloud of positively charged ions 156 are repelled from the dissociated, upstream discharge electrode 150 and from one another due to their common charge thereby forming a corona wind, or cloud of positively charged ions 156, through a dielectric conduit, or pathway 158.

An exit end 160 of the annular pathway 158 merges with an outlet port 162 of an encompassed air passage 164, which contains the spray nozzle 154, to form an exit 166 of an inhaler device (not shown in FIGS. 16-19). An aerosol of negatively charged, aerosolized liquid particles are sprayed from the spray nozzle 154 as described above in the encompassed air passage 164. The corona of positively charged ions 156 neutralizes the aerosol by interacting at this exit 166.

The dissociated, upstream discharge electrode 150 is electrically dissociated from the spray nozzle 154 and thus does not impair its EHD operation. Instead a strong relationship (i.e., electrical attraction) between each EHD nozzle tip 170 of the spray nozzle 154 and the cloud of positively charged ions 156. In addition to aiding EHD spraying, the cloud of positively charged ions 156 influences the motion and direction of the aerosol after the negatively charged particles are formed at each EHD nozzle tip 170 and begin to diverge from one another. Because of its location and direction of motion relative to pathway 158, the negatively charged particles of aerosol are directed toward the outlet port 162 of encompassed air passage 164 and toward the exit 166 of the inhaler device in an axial flow manner rather than a cross flow manner, minimizing wetting.

Figure 18:
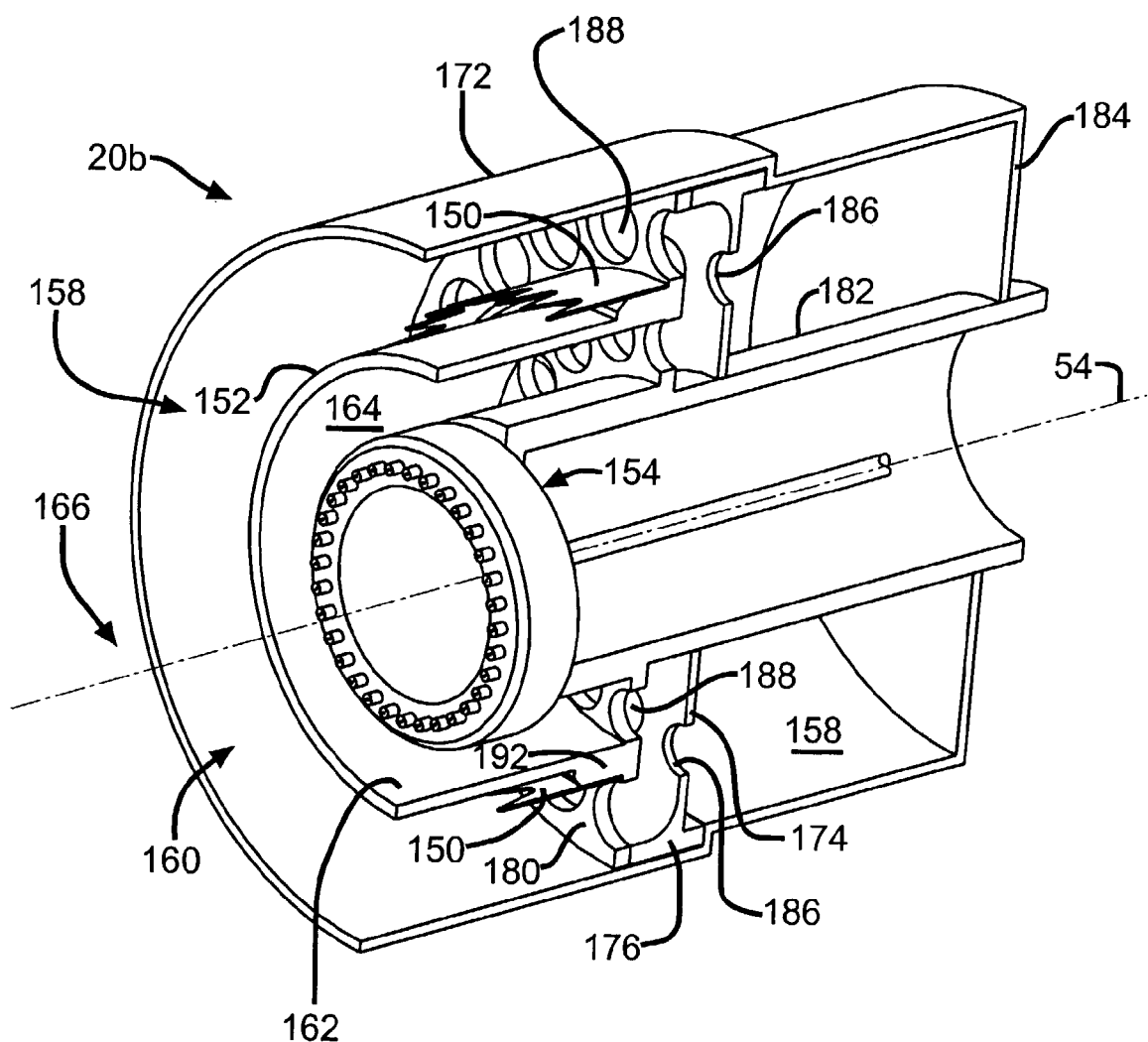
FIG. 18 depicts a longitudinally cross-sectioned pictorial of the DDS multiple-tip EHD nozzle assembly shown in FIG. 16.
Figure 19:
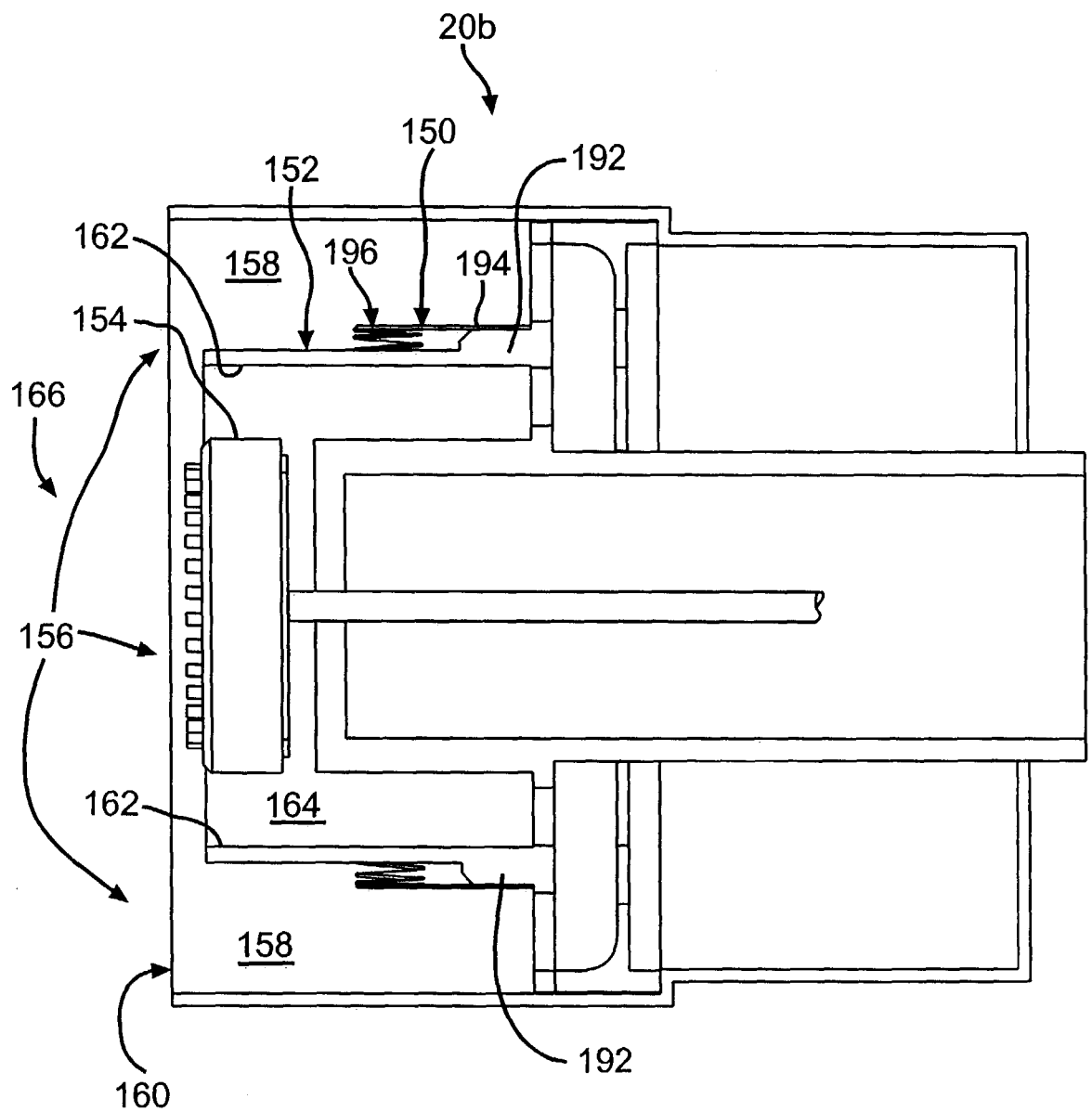
FIG. 19 depicts an elevational cross section view of the DDS multiple-tip EHD nozzle assembly shown in FIG. 16.

In the illustrative embodiment, the DDS EHD nozzle assembly 20b further comprises a stepped, base mounting cylinder 172 having positioned therein a base plate 174. Base plate 174 includes an integral, circumferential rim 176 and is positioned within stepped, base mounting cylinder 172 by integral, circumferential rim 176, as best illustrated in FIG. 19. A discharge electrode support cylinder 178 formed integral with positioning flange 180 and a central tube 182, is positioned within the stepped, base mounting cylinder 172 as illustrated best in FIG. 19. As illustrated in FIGS. 18-19, central tube 182 extends through base plate 174 and a rear wall 184 of stepped, base mounting cylinder 172 thereby stabilizing discharge electrode support cylinder 178 symmetrically within the stepped, base mounting cylinder 172. As seen in FIG. 19, the integral, circumferential rim 176 of base plate 174 acts as an axial spacer between base plate 174 and positioning flange 180. Base plate 174 and positioning flange 180 include a multiplicity of apertures 186 and 188, respectively. Apertures 186 and 188 permit the axial flow of air into the rear of both the annular pathway 158 and the encompassed air passage 164 during inhalation by the user of the inhaler device. A suitable ventilation opening 190 is provided at the rear of mounting cylinder 172 to permit the introduction of air into the DDS EHD nozzle assembly 20b.

Juxtaposed positioning flange 180 and circumscribing discharge electrode support cylinder 178 is an area of enlarged diameter 192 receiving thereon a circumscribing electrode band 194 of the dissociated, upstream discharge electrode 150. Projecting axially forward from the circumscribing electrode band 194 are a multiplicity of, cusp like, sharply pointed discharge electrode spikes 196. As illustrated in FIGS. 18-19, discharge electrode spikes 196 extend axially forward from the area of increased diameter 192 whereby discharge electrode spikes 196 are suspended above discharge electrode support cylinder 178. The circumscribing electrode band 194 is affixed to positioning flange 180 by three, or more, tangs 198 which extend through slotted openings 200 and are bent 90 degrees over the back side of positioning flange 180 thereby securing circumscribing electrode band 194 to positioning flange 180.

The illustrated stainless steel band lends itself to economical fabrication and assembly of the plurality of discharge electrodes. As depicted, the plurality of discharge electrodes were regularly spaced points with a generally rectangular cutout from the discharge band forming the spacing therebetween. It should be appreciated that a discharge band may be used in some applications with other shapes and spacing of discharge electrodes. For instance, a sawtooth pattern or a scalloped pattern may be used to achieve the desired discharge electrical field. Furthermore, in applications wherein the nozzle tips and discharge band are not circularly arranged, it may be desirable to vary the spacing of the discharge electrodes to accommodate the change in geometry (e.g., variance in distance from each discharge electrode to the nearest nozzle tips).

It will be appreciated that a circular cross section encompassed air passage 164 surrounded by a discharge electrode chamber 148 is illustrative. Aspects of the present invention may be realized by cross sectional shapes other than circular, such as oval or square. In addition, rather than an ion cloud annularly surrounding the aerosolized liquid, a ring of spray sites may be annularly ducted around a central passage that produces an ion cloud. In addition, side-by-side passages for the aerosolized liquid and ion cloud may be provided with neither surrounding fully the other.

Operation of Handheld EHD Inhaler. In use, the pulmonary delivery device 10 is held by the user in any convenient orientation so that the exit opening is to the user's mouth. The user activates the control circuit 22, which activates the dispensing system 18 to direct stored liquid to the spray nozzle 28 in the EHD nozzle assembly 20. Grooved channels 74 in the spray nozzle advantageously provide a consistent fluid pressure drop to the circumferentially arranged nozzle tips 32, thereby allowing the spray nozzle 28 to operate consistently at angles other than vertical. The spray nozzle 28 is given an electrical charge by the portable power supply 16. This electrical charge may be delivered at the nozzle tips 32. Alternatively, the tips 90 may be formed of a dielectric material having a low surface energy that reduces wicking with the electrical charge imparted to the liquid upstream. The aerosolized liquid is directed toward a downstream opening of the spray passage 50. The discharge electrode tips 48 or a cloud of oppositely-charged ions are presented annularly around the downstream opening to neutralize the aerosolized liquid. Most or all of the elongated discharge electrodes 26 are shielded from the spray passage 50 by a dielectric discharge shield 30 that presents a long path between elongated discharge electrodes 26 and the spray nozzle 28 that is unlikely to be wetted by the aerosolized liquid.

By virtue of the foregoing, an improved EHD nozzle achieves high dose rate (microliters/minute) with low wetting and small particle size (1.0-5 microns), although these properties tend to be mutually exclusive. Furthermore, these attributes are incorporated into a conveniently small, handheld device.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art. For example, although the EHD nozzle assemblies 20, 20a, 20b are particularly useful in portable devices, it will be appreciated that aspects of the current invention are applicable to fixed units. In addition, although dispensing of therapeutic liquids is illustrated, it will be appreciated that a wide range of liquids and mixtures may be electrohydrodynamically sprayed consistent with aspects of the present invention.

What is claimed is:

1. An apparatus for electrohydrodynamic spraying having a power source and further comprising:
   a shroud defining a spray passage having a longitudinal axis, defined by downstream and upstream ends;
   a spray nozzle comprising at least one spray site and a liquid supply passage having a liquid to be aerosolized contained therein, said nozzle configured to aerosolize liquid received from the liquid supply passage and to release charged aerosol particles toward the downstream end of said longitudinal axis;
   a discharge electrode positioned upstream of said spray site and comprising at least one discharge point, said electrode shielded from said aerosolized liquid by said shroud being positioned between said at least one spray site and said at least one discharge point and configured to produce a cloud of positively charged ions when a voltage is applied thereto;
   wherein said power source is operatively connected to said discharge electrode; and wherein said power source is operatively connected to said nozzle, spray site, liquid supply passage, or to a metal electrode in liquid supply passage.

2. The apparatus of claim 1, wherein the spray nozzle further comprises:
   a forward surface directed toward the downstream opening of said longitudinal axis;
   a plurality of spray sites arrayed about the forward surface; and
   a plurality of channels each communicating between the liquid supply passage and a respective spray site, each channel configured to present a selected pressure drop for mitigating gravitational effects of orientation of the longitudinal axis of the spray nozzle.

3. The apparatus of claim 2, wherein the plurality of spray sites are circumferentially arranged and the plurality of channels comprises sprue like symmetrical branches, each channel having an equivalent cross sectional area, length and number of turns to achieve a comparable pressure at each spray site.

4. The apparatus of claim 2, wherein the spray sites are formed from a dielectric material and the liquid supply passage is operatively connected to said power source so as to impart a charge to said liquid.

5. The apparatus of claim 1, wherein the discharge electrode comprises a circumscribing band having a multiplicity of sharply pointed cusps or spikes.

6. The apparatus of claim 1, wherein the nozzle is configured to present a selected pressure drop for mitigating gravitational effects of orientation of the longitudinal axis of the spray nozzle.

7. The apparatus of claim 1, wherein the aerosolized liquid is electrically neutralized in order to reach a patient's lungs.

8. A pulmonary aerosol delivery device, comprising an electrohydrodynamic spraying apparatus having a power supply and further comprising:
   a shroud defining a spray passage having a longitudinal axis, defined by upstream and downstream ends, the shroud having a downstream opening on the longitudinal axis;
   a cover annularly encompassing the shroud to form a dielectric pathway there between;
   a discharge electrode positioned within the dielectric pathway, said discharge electrode operatively connected to said power supply and configured to produce a cloud of charged ions when voltage is applied thereto;
   a spray nozzle contained in said spray passage having a liquid passage and a spray site configured to deliver aerosolized liquid received from the liquid passage toward the downstream end of said longitudinal axis, said nozzle, spray site or liquid passage operatively connected to said power supply so as to produce charged particles of aerosol;
   a dispensing system for containing the therapeutic liquid to be aerosolized and delivering the therapeutic liquid to the electrohydrodynamic apparatus;
   a control circuit communicating with the dispensing system, the electrohydrodynamic apparatus, and the power supply;
   a housing of such size that the housing can be held in a user's one hand, the housing having an exit opening for directing the aerosolized therapeutic liquid to a user's mouth and included in said housing the electrohydrodynamic apparatus, dispensing system, power supply and control circuit; and
   wherein said discharge electrode is positioned upstream of said spray site and shielded from said aerosolized liquid by said shroud being positioned between said spray site and said discharge electrode.

9. The device of claim 8, wherein the spray nozzle further comprises:
   a forward surface directed toward the downstream opening of the spray passage;
   a plurality of spray sites arrayed about the forward surface; and
   a plurality of channels each communicating between the liquid passage and a respective spray site, each channel configured to present a selected pressure drop for mitigating gravitational effects of orientation of the longitudinal axis of the spray nozzle.

10. The device of claim 9, wherein the plurality of spray sites are circumferentially arranged and the plurality of channels comprises sprue like symmetrical branches, each channel having an equivalent cross sectional area, length and number of turns to achieve a comparable pressure at each spray site.

11. The device of claim 9, wherein each channel is configured to present a selected pressure drop for mitigating gravitational effects of orientation of the longitudinal axis of the spray nozzle.

12. The device of claim 8, wherein the discharge electrode comprises a circumscribing band having a multiplicity of sharply pointed cusps or spikes.

13. The device of claim 8, wherein the spray site of the spray nozzle is formed from a dielectric material, and the liquid passage is operatively connected to said power supply to provide a negative charge to said liquid passage so as to produce a negative charge on said liquid and to produce negatively charged particles of aerosol.

14. The device of claim 8, wherein the nozzle is configured to present a selected pressure drop for mitigating gravitational effects of orientation of the longitudinal axis of the spray nozzle.

15. The device of claim 8, wherein the aerosolized liquid is electrically neutralized in order to reach a patient's lungs.

16. An apparatus for electrohydrodynamically spraying having a power source, comprising:
   a dielectric cover;
   a dielectric shroud within the cover longitudinally separating an electrode cavity and a spray passage;
   a spray nozzle contained in the spray passage and having a liquid passage and one or more spray sites configured to aerosolize liquid received from the liquid passage;

wherein said power source is capable of providing an electric field of sufficient strength to produce a Taylor Cone and aerosolize liquid at the spray site(s);

an electrode contained within the electrode cavity upstream of a plane formed by the spray site(s) of the spray nozzle, the electrode operatively connected to said power source and configured to produce an ion cloud of air within the electrode cavity;

wherein said shroud is positioned between said one or more spray sites and said electrode.

17. The apparatus of claim 16, wherein the spray nozzle comprises:

a forward surface directed toward the downstream opening of the spray passage;

a plurality of spray sites arrayed the forward surface; and a plurality of channels communicating between the liquid passage and a respective spray site, each channel configured to present a selected pressure drop for mitigating gravitational effects of orientation of the longitudinal axis of the spray nozzle.

18. The apparatus of claim 17, wherein the plurality of spray sites are circumferentially arranged and the plurality of channels comprises sprue like symmetrical branches, each channel having an equivalent cross sectional area, length and number of turns to achieve a comparable pressure at each spray site.

19. The apparatus of claim 18, wherein the spray site of the spray nozzle is formed from a dielectric material and the liquid passage of the spray passage is operatively connected to said power source upstream of said spray site.

20. The apparatus of claim 16, wherein the nozzle is configured to present a selected pressure drop for mitigating gravitational effects of orientation of the longitudinal axis of the spray nozzle.

21. The apparatus of claim 16, wherein the aerosolized liquid is electrically neutralized in order to reach a patient's lungs.

22. An apparatus for electrohydrodynamic spraying having a power source and further comprising:

a shroud defining a spray passage having a longitudinal axis defined by upstream and downstream ends, the shroud having a downstream opening on the longitudinal axis;

a cover annularly encompassing the shroud to form a dielectric pathway there between;

a discharge electrode having at least one discharge point positioned within the dielectric pathway, said discharge electrode operatively connected to said power source and configured to produce a cloud of positively charged ions when a voltage is provided thereto;

a spray nozzle contained in the spray passage having a liquid passage and at least one spray site, said nozzle configured to deliver aerosolized liquid received from the liquid passage toward the downstream end of the longitudinal axis, said nozzle operatively connected to said power source and configured to produce a charge on said liquid opposite the charge on the discharge electrode;

wherein said discharge electrode is positioned upstream of said spray site and shielded from said aerosolized liquid by said shroud being positioned between said at least one spray site and said at least one discharge point.

23. The apparatus of claim 22, wherein the spray nozzle has more than one spray site.

24. The apparatus of claim 23, wherein the spray nozzle further comprises a plurality of channels communicating between the liquid passage and a respective spray site, each channel configured to present a selected pressure drop for mitigating gravitational effects of orientation of the longitudinal axis of the spray nozzle.

25. The apparatus of claim 23, wherein the more than one spray sites are circumferentially arranged and the plurality of channels comprises sprue like symmetrical branches.

26. The apparatus of claim 22, wherein the nozzle is configured to present a selected pressure drop for mitigating gravitational effects of orientation of the longitudinal axis of the spray nozzle.

27. The apparatus of claim 22, wherein the aerosolized liquid is electrically neutralized in order to reach a patient's lungs.

* * * * *